US012642473B2

(12) United States Patent
Qu

(10) Patent No.: US 12,642,473 B2
(45) Date of Patent: Jun. 2, 2026

(54) METHODS AND APPARATUSES TO DETECT TACHYCARDIAS AND SELECTIVELY REJECT TACHYCARDIA DETECTIONS

(71) Applicant: Pacesetter, Inc., Sylmar, CA (US)

(72) Inventor: Fujian Qu, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 471 days.

(21) Appl. No.: 18/164,251

(22) Filed: Feb. 3, 2023

(65) Prior Publication Data

US 2023/0293085 A1    Sep. 21, 2023

Related U.S. Application Data

(60) Provisional application No. 63/320,165, filed on Mar. 15, 2022.

(51) Int. Cl.
| | |
|---|---|
| *A61B 5/36* | (2021.01) |
| *A61B 5/00* | (2006.01) |
| *A61B 5/352* | (2021.01) |
| *A61B 5/355* | (2021.01) |
| *A61B 5/363* | (2021.01) |

(52) U.S. Cl.
CPC ............. *A61B 5/363* (2021.01); *A61B 5/352* (2021.01); *A61B 5/355* (2021.01); *A61B 5/7225* (2013.01)

(58) Field of Classification Search
None
See application file for complete search history.

(56) References Cited

U.S. PATENT DOCUMENTS

| | | | |
|---|---|---|---|
| 2008/0082014 A1* | 4/2008 | Cao ...................... | A61B 5/7264 600/509 |
| 2015/0208938 A1* | 7/2015 | Houben ................ | A61B 5/363 600/509 |
| 2019/0184164 A1* | 6/2019 | Zhang ................... | A61B 5/352 |
| 2020/0357518 A1* | 11/2020 | Musgrove .............. | A61B 5/361 |

* cited by examiner

*Primary Examiner* — Ankit D Tejani
(74) *Attorney, Agent, or Firm* — Pearl Cohen Zedek Latzer Baratz LLP

(57) ABSTRACT

Described herein are apparatuses and methods to detect tachycardias and selectively reject false tachycardia detections due to T-wave oversensing or noise. An apparatus includes electrodes, a sensing circuit coupled to at least two of the electrodes and configured to sense a signal indicative of cardiac electrical activity, and a smoothing filter configured to filter to the sensed signal indicative of cardiac electrical activity to thereby produce a filtered signal indicative of cardiac electrical activity. The apparatus produces a difference signal indicative of cardiac electrical activity by determining a difference between the sensed and filtered signals indicative of cardiac electrical activity. The apparatus also includes at least one processor configured to detect a tachycardia, or to determine whether or not to reject a tachycardia detection, based on the difference signal. The smoothing filter and/or difference circuitry can be implemented by the at least one processor, and/or other circuitry.

23 Claims, 12 Drawing Sheets

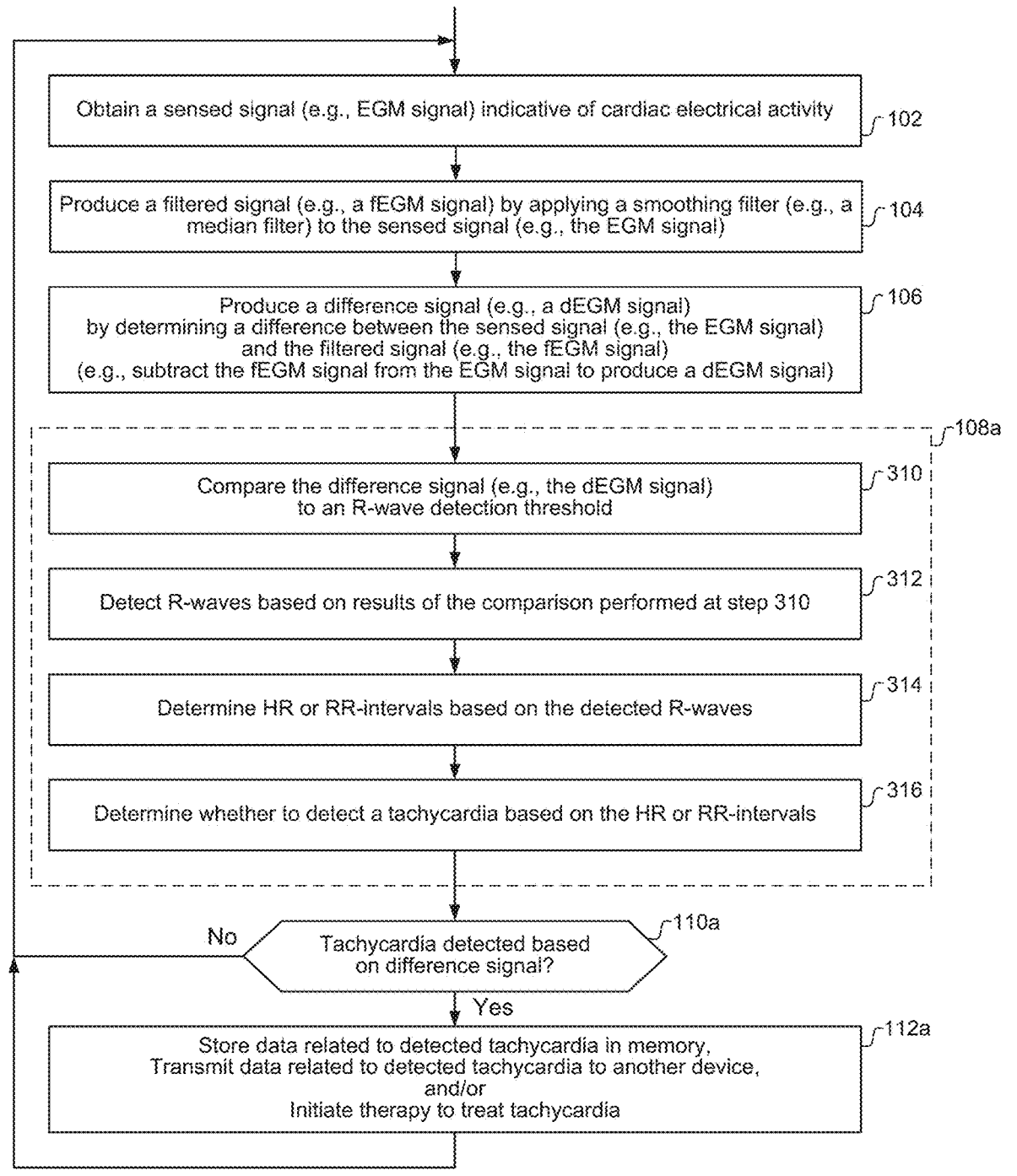

Obtain a sensed signal (e.g., EGM signal) indicative of cardiac electrical activity — 102

Produce a filtered signal (e.g., a fEGM signal) by applying a smoothing filter (e.g., a median filter) to the sensed signal (e.g., the EGM signal) — 104

Produce a difference signal (e.g., a dEGM signal) by determining a difference between the sensed signal (e.g., the EGM signal) and the filtered signal (e.g., the fEGM signal) (e.g., subtract the fEGM signal from the EGM signal to produce a dEGM signal) — 106

108a

Compare the difference signal (e.g., the dEGM signal) to an R-wave detection threshold — 310

Detect R-waves based on results of the comparison performed at step 310 — 312

Determine HR or RR-intervals based on the detected R-waves — 314

Determine whether to detect a tachycardia based on the HR or RR-intervals — 316

No ← Tachycardia detected based on difference signal? — 110a
↓ Yes

Store data related to detected tachycardia in memory, Transmit data related to detected tachycardia to another device, and/or Initiate therapy to treat tachycardia — 112a

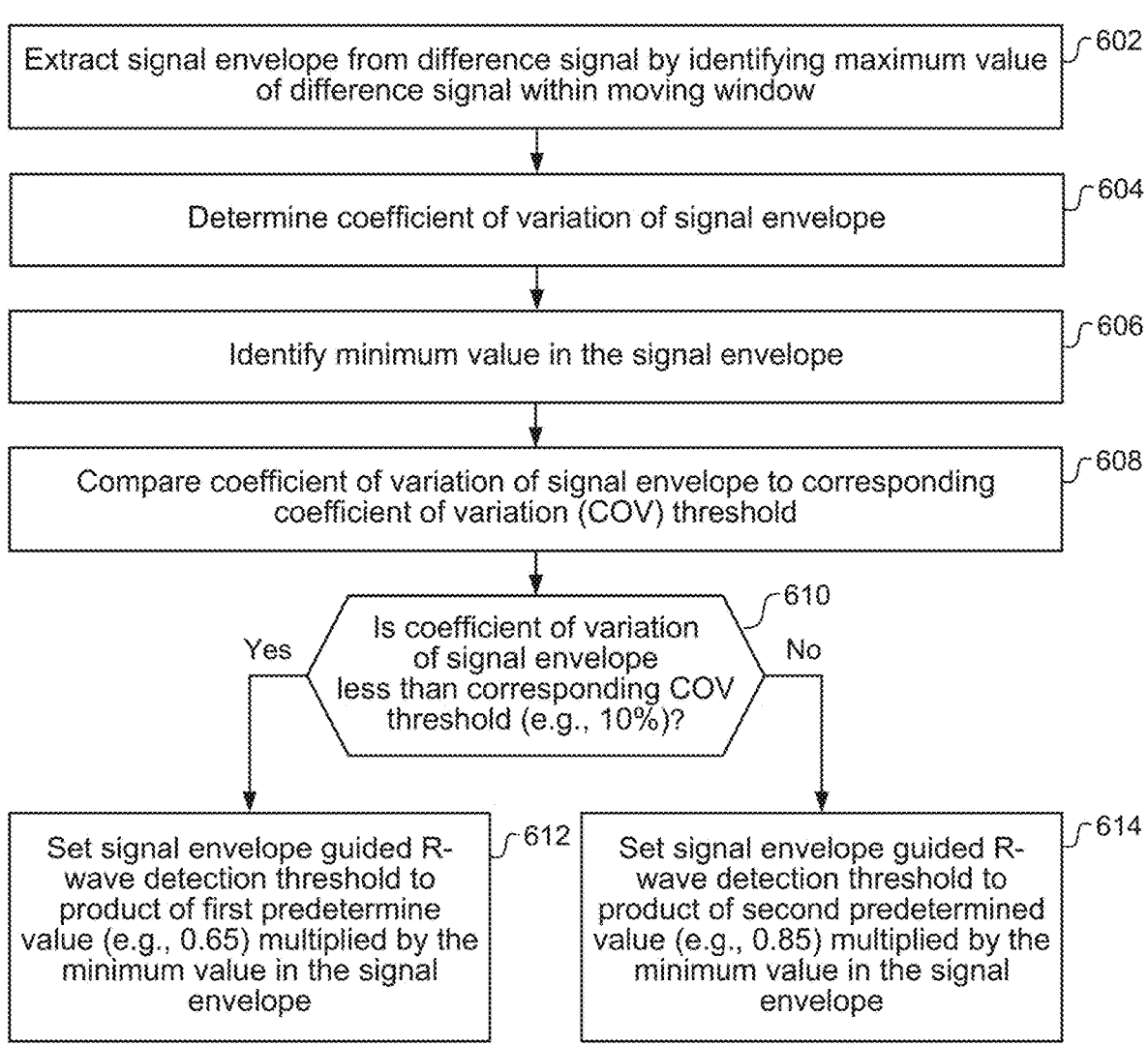

Extract signal envelope from difference signal by identifying maximum value of difference signal within moving window ⌐602

Determine coefficient of variation of signal envelope ⌐604

Identify minimum value in the signal envelope ⌐606

Compare coefficient of variation of signal envelope to corresponding coefficient of variation (COV) threshold ⌐608

Is coefficient of variation of signal envelope less than corresponding COV threshold (e.g., 10%)? ⌐610

Yes          No

Set signal envelope guided R-wave detection threshold to product of first predetermine value (e.g., 0.65) multiplied by the minimum value in the signal envelope ⌐612

Set signal envelope guided R-wave detection threshold to product of second predetermined value (e.g., 0.85) multiplied by the minimum value in the signal envelope ⌐614

*FIG. 6*

METHODS AND APPARATUSES TO DETECT TACHYCARDIAS AND SELECTIVELY REJECT TACHYCARDIA DETECTIONS

PRIORITY CLAIM

This application claims priority to U.S. Provisional Patent Application No. 63/320,165, filed Mar. 15, 2022.

FIELD

Embodiments of the present technology generally relate to implantable medical devices, and methods and systems for use therewith, that can be used to detect tachycardias and selectively reject tachycardia detections.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias or bradycardias, and those that result in a faster heart rate than normal are called tachyarrhythmias or tachycardias. Tachyarrhythmias are further classified as supraventricular tachyarrhythmias (SVTs) and ventricular tachyarrhythmia (VT). SVTs are generally characterized by abnormal rhythms that may arise in the atria or the atrioventricular node (AV node). Additionally, there are various types of different SVTs and various types of VTs that can be characterized. For example, a paroxysmal SVT can exhibit heart rates between approximately 140 beats per minute (bpm) and approximately 250 bpm. However, the most common SVTs are typically atrial flutter (AFL) and atrial fibrillation (AF). In addition, many SVTs involve the AV node, for example, AV nodal reentry tachycardia (AVNRT) where an electrical loop or circuit includes the AV node. Another type of SVT is an AV reentrant tachycardia (AVRT), where an AV reentrant circuit typically involves the AV node and an aberrant conducting bundle known as an accessory pathway that connects a ventricle to an atrium.

AFL can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even HF as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing AF. AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of 100 bpm or more. Such activity may degenerate further into disorganized electrical activity known as VF. In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia. Further, there are various different types of VT, including, e.g., monomorphic VT and polymorphic VT.

Where an implantable medical device (IMD) is used to monitor for arrythmias, it is often important for the IMD to be able distinguish false positive arrhythmia detections from true positive detections, as well as to distinguish between different types of arrythmias. For example, where an IMD is capable of performing therapy, it is important that detected arrythmias are properly classified so that appropriate types of therapy can be delivered in order to convert the arrythmias back to NSR, as the therapy for treating a VT will differ from the therapy for treating an SVT. For another example, where the IMD is a monitoring device that is not capable of performing therapy, it is important that detected arrythmias are properly classified so that an underlying condition of a patient can be properly identified, which can thereby enable appropriate medication and/or an appropriate IMD to be identified to treat the underlying condition moving forward. Additionally, rejecting falsely detected arrhythmias and properly classifying arrythmias reduces the clinical burden associated with clinicians reviewing electrograms (EGMs) and other cardiac information stored by an IMD. An example type of IMD that performs monitoring, but is not capable of performing therapy, and which would benefit from accurate arrythmia detection, rejection and/or discrimination, is an insertable cardiac monitor (ICM). Example types of IMD that perform therapy and would benefit for accurate arrhythmia detection and discrimination include an implantable cardioverter-defibrillator (ICD) and a cardiac pacemaker. Such a cardiac pacemaker can be of the type that includes a "can" or housing from which one or more leads extend, or a leadless cardiac pacemaker (LCP).

When an IMD detects an arrhythmic episode, information about the episode may be recorded and a corresponding EGM segment (and/or other information) can be transmitted from the IMD to a patient care network for clinician review. False positive arrhythmia detections are highly undesirable, as the burden of sorting through large numbers of clinically irrelevant episodes of arrythmias can be time consuming and costly. Additionally, misclassified arrythmia detections are also undesirable, as the burden of sorting through and correcting misclassifications can also be time consuming and costly. Further, where an IMD is capable of delivering therapy, a false positive arrhythmia detection can lead to inappropriate therapy, which is undesirable.

SUMMARY

In accordance with certain embodiments of the present technology, an apparatus comprises a plurality of electrodes, a sensing circuit coupled to at least two of the electrodes and configured to sense a signal indicative of cardiac electrical activity, and a smoothing filter configured to filter to the sensed signal indicative of cardiac electrical activity to thereby produce a filtered signal indicative of cardiac electrical activity. The apparatus also comprises difference circuitry configured to produce a difference signal indicative of cardiac electrical activity by determining a difference between the sensed signal indicative of cardiac electrical activity and the filtered signal indicative of cardiac electrical activity. Additionally, the apparatus comprises at least one processor configured to detect a tachycardia based on the difference signal, or configured to determine whether or not to reject a tachycardia detection based on the difference signal. The smoothing filter can be implemented by the at least one processor, or by circuitry that is separate from the at least one processor, depending upon the specific implementation. The difference circuitry can be implemented by the at least one processor or, by circuitry that is separate from the at least one processor, depending upon the specific implementation. The apparatus can be an implantable medical device (IMD). Alternatively, the apparatus can be a non-implantable device, such as, but not limited to an external programmer. It is also possible that the apparatus is a distributed apparatus, e.g., a system. The smoothing filter can be, for example, a median filter, but is not limited thereto.

In accordance with certain embodiments of the present technology, the apparatus also includes a memory and a telemetry circuit. In certain such embodiments, the at least one processor is configured to detect a tachycardia based on the difference signal, and in response to the tachycardia being detected, the at least one processor is configured to store or maintain data related to the tachycardia in the memory, cause the telemetry circuit to transmit data related to the tachycardia to another apparatus and/or initiate delivery of tachycardia therapy using at least one of the plurality of electrodes. In certain such embodiments, the at least one processor is configured determine whether or not to reject a tachycardia detection based on the difference signal, and in response to the tachycardia detection being rejected, the at least one processor is configured to allow data related to the tachycardia stored in the memory to be overwritten, prevent the telemetry circuit from transmitting data related to the tachycardia to another apparatus, and/or withhold or terminate tachycardia therapy.

In accordance with certain embodiments, the sensed signal indicative of cardiac electrical activity comprises a sensed electrogram (EGM) signal, and the filtered signal comprises a filtered EGM (fEGM) signal. In such embodiments, the smoothing filter is configured to filter to the EGM signal to produce the filtered EGM (fEGM) signal, and the difference circuitry is configured to produce a difference EGM (dEGM) signal indicative of cardiac electrical activity by determining a difference between the sensed EGM signal and fEGM signal. Further, the at least one processor is configured to detect a tachycardia based on the dEGM signal, or configured to determine whether or not to reject a tachycardia detection based on the dEGM signal.

In accordance with certain embodiments, the at least one processor is configured to compare an amplitude of the difference signal to an R-wave detection threshold to thereby detect R-waves, determine a heart rate (HR) or R-R intervals based on the detected R-waves, and detect the tachycardia based on the HR or the RR-intervals.

In accordance with certain embodiments, the at least one processor is configured to compare an amplitude of the sensed signal indicative of cardiac electrical activity to an R-wave detection threshold to thereby detecting R-waves, determine a heart rate (HR) or R-R intervals based on the detected R-waves, and detect a tachycardia based on the HR or the RR-intervals. Additionally, the at least one processor is configured to determine whether or not to reject tachycardia detection based on the difference signal by determining whether the tachycardiac detection was likely due to at least one of T-wave oversensing or noise.

In accordance with certain embodiments, in order to the determine whether or not to reject the tachycardia detection based on the difference signal, the at least one processor is configured to, for each detected R-wave of a plurality of the detected R-waves: determine a peak amplitude ratio for the detected R-wave by dividing an absolute value of a peak amplitude of the R-wave within the difference signal by an absolute value of a peak amplitude of the detected R-wave within the sensed signal; compare the peak amplitude ratio to a corresponding peak amplitude ratio (PAR) threshold; and when the peak amplitude ratio is less than the corresponding PAR threshold, analyze windows of the difference signal before and after the detected R-wave to determine whether or not to classify the detected R wave as being falsely detected due to T-wave oversensing. In such embodiments, the at least one processor is also configured to determine whether or not to reject the tachycardia detection based on an amount of the detected R-waves that were classified as being falsely detected due to T-wave oversensing.

In accordance with certain embodiments, for a detected R-wave, in order to analyze windows of the difference signal before and the detected R-wave to determine whether or not to classify the detected R wave as being falsely detected due to T-wave oversensing, the at least one processor is configured to: compare a first window of the difference signal immediately preceding the detected R-wave to a second window of the difference signal immediately following the detected R-wave to determine which one of the first and the second windows has a larger peak amplitude; count a number of reversal points in the one of the first and the second windows of the difference signal that has the larger peak amplitude in the difference signal; compare the number of reversal points to a corresponding number of reversal points (NRP) threshold; and determine whether or not to classify the R-wave as being falsely detected due to T-wave oversensing based on results of the comparing the number of reversal points to the corresponding NRP threshold.

In accordance with certain embodiments, in order to determine whether or not to reject the tachycardia detection based on an amount of the detected R-waves that were classified as being falsely detected due to T-wave oversensing, the at least one processor is configured to compare an amount of the detected R-waves, that were initially used to detect the tachycardia and were thereafter classified as being falsely detected due to T-wave oversensing, to a corresponding T-wave oversensing threshold. Additionally, the at least one processor is configured to reject the tachycardia detection in response to the amount of the R-waves classified as being falsely detected due to T-wave oversensing equaling or exceeding the corresponding T-wave oversensing threshold.

In accordance with certain embodiments, the at least one processor is further configured to mark or classify a tachycardia detection as potentially being a ventricular tachycardia (VT) when at least two consecutive ones of the detected R-waves are classified as being falsely detected due to T-wave oversensing.

In accordance with certain embodiments, in response to none of the R-waves being classified as being falsely detected due to T-wave oversensing, the at least one processor is configured to determine a signal envelope guided R-wave detection threshold, redetect R-waves in the difference signal by comparing the amplitude of the difference signal to the signal envelope guided R-wave detection threshold, determine a redetected heart rate (HR) or redetected R-R intervals based on the redetected R-waves, and determine whether or not to reject the tachycardia detection based on the redetected HR or the redetected R-R intervals. In certain such embodiments, in order to determine whether or not to reject the tachycardia detection based on the redetected HR or the redetected R-R intervals, the at least one processor is configured to compare the redetected HR or an average of the redetect R-R intervals to a corresponding threshold indicative of the redetected HR being too slow to be an actual tachycardia, and selectively reject the tachycardia detection based on results of the comparing the redetected HR or the average of the redetect R-R intervals to the corresponding threshold indicative of the redetected HR being too slow to be a tachycardia.

In accordance with certain embodiments, in order to determine the signal envelope guided R-wave detection threshold, the at least one processor is configured to extract a signal envelope from the difference signal by identifying a maximum value of the difference signal within a moving window, determine a coefficient of variation of the signal envelope, identify a minimum value in the signal envelope, and compare the coefficient of variation of the signal envelope to a corresponding coefficient of variation (COV) threshold. Additionally, the at least one processor is configured to set the signal envelope guided R-wave detection threshold to a product of a first predetermine value multiplied by the minimum value in the signal envelope, when the coefficient of variation is less than the corresponding COV threshold. By contrast, the at least one processor is configured to set the signal envelope guided R-wave detection threshold to a product of a second predetermined value multiplied by the minimum value in the signal envelope, when the coefficient of variation is greater than the corresponding COV threshold, wherein the second predetermined value is greater than the first predetermined value.

In accordance with certain embodiments, in response to none of the R-waves being classified as being falsely detected due to T-wave oversensing, the at least one processor is configured to determine a minimal sensed R-wave amplitude guided threshold, redetect R-waves in the difference signal by comparing the amplitude of the difference signal to the minimal sensed R-wave amplitude guided threshold, determine a redetected heart rate (HR) or redetected R-R intervals based on the redetected R-waves, and determine whether or not to reject the tachycardia detection based on the redetected HR or the redetected R-R intervals. In certain such embodiments, in order to determining whether or not to reject the tachycardia detection based on the redetected HR or the redetected R-R intervals, the at least one processor is configured to compare the redetected HR or an average of the redetect R-R intervals to a corresponding threshold indicative of the redetected HR being too fast to be an actual tachycardia, and selectively reject the tachycardia detection based on results of the comparing the redetected HR or the average of the redetect R-R intervals to the corresponding threshold indicative of the redetected HR being too fast to be an actual tachycardia.

In accordance with certain embodiments, the at least one processor is configured to determine the minimal sensed R-wave amplitude guided threshold by identifying a smallest R-wave peak in the difference signal, and setting the minimal sensed R-wave amplitude guided threshold to a value that is less than the smallest R-wave peak in the difference signal. In certain such embodiments, when redetecting R-waves in the difference signal, by comparing the amplitude of the difference signal to the minimal sensed R-wave amplitude guided threshold, a length of a refractory period that is used for the redetecting is less than a length of a refractory period that is used to initially detect R-waves when comparing the amplitude of the sensed signal indicative of cardiac electrical activity to the R-wave detection threshold.

Certain embodiments of the present technology are directed to methods for improving tachycardia detections, as well as to methods for rejecting falsely detected tachycardia. In accordance with certain embodiments, such a method comprises obtaining a sensed signal indicative of cardiac electrical activity (e.g., an EGM signal), producing a filtered signal (e.g., an fEGM signal) indicative of cardiac electrical activity by applying a smoothing filter to the sensed signal indicative of cardiac electrical activity, and producing a difference signal (e.g., a dEGM signal) indicative of cardiac electrical activity by determining a difference between the sensed signal indicative of cardiac electrical activity and the filtered signal (e.g., the fEGM signal) indicative of cardiac electrical activity. The method also comprises detecting a tachycardia based on the difference signal (e.g., the dEGM signal), or determining whether or not to reject a tachycardia detection based on the difference signal (e.g., the dEGM signal). The smoothing filter can be, e.g., a median filter, as noted above, in which case producing the filtered signal indicative of cardiac electrical activity can be achieved by applying the median filter to the sensed signal indicative of cardiac electrical activity.

In accordance with certain embodiments, where the method comprises detecting a tachycardia based on the difference signal, the method further comprises performing one or more of the following in response to the tachycardia being detected: storing or maintaining data related to the tachycardia in memory, causing transmitting of data related to the tachycardia to another apparatus and/or initiating delivery of tachycardia therapy.

In accordance with certain embodiments, where the method comprises determining whether or not to reject a tachycardia detection based on the difference signal, the method further comprises performing one or more of the following in response to the tachycardia detection being rejected: allowing data related to the tachycardia stored in memory to be overwritten, preventing transmitting of data related to the tachycardia to another apparatus and/or withholding or terminating tachycardia therapy.

In accordance with certain embodiments, detecting a tachycardia based on the difference signal can be achieved by comparing an amplitude of the difference signal to an R-wave detection threshold, detecting R-waves based on results of the comparing, determining a heart rate (HR) or R-R intervals based on the detected R-waves, and detecting the tachycardia based on the HR or the RR-intervals.

In accordance with certain embodiments, a tachycardia is detected based on the sensed signal indicative of cardiac electrical activity by comparing an amplitude of the sensed signal indicative of cardiac electrical activity to an R-wave detection threshold, detecting R-waves based on results of the comparing, determining a heart rate (HR) or R-R intervals based on the detected R-waves, and detecting the tachycardia based on the HR or the RR-intervals. In certain embodiments, the filtered signal and the difference signal are produced in response to the tachycardia being detected, and determining whether or not to reject the tachycardia detection can be based on the difference signal by determining whether the tachycardiac detection was likely due to at least one of T-wave oversensing or noise.

In accordance with certain embodiments, the determining whether or not to reject the tachycardia detection based on the difference signal comprises for each detected R-wave of a plurality of the detected R-waves: determining a peak amplitude ratio for the detected R-wave by dividing an absolute value of a peak amplitude of the R-wave within the difference signal by an absolute value of a peak amplitude of the detected R-wave within the sensed signal; comparing the peak amplitude ratio to a corresponding peak amplitude ratio (PAR) threshold; and when the peak amplitude ratio is less than the corresponding PAR threshold, analyzing windows of the difference signal before and after the detected R-wave to determine whether or not to classify the detected R wave as being falsely detected due to T-wave oversensing. Such a method can also include determining whether or not to reject the tachycardia detection based on an amount of the detected R-waves that were classified as being falsely detected due to T-wave oversensing.

In accordance with certain embodiments, the method can further comprise for a detected R-wave, in order to analyze windows of the difference signal before and after the detected R-wave to determine whether or not to classify the detected R wave as being falsely detected due to T-wave oversensing: comparing a first window of the difference signal immediately preceding the detected R-wave to a second window of the difference signal immediately following the detected R-wave to determine which one of the first and the second windows has a larger peak amplitude; counting a number of reversal points in the one of the first and the second windows of the difference signal that has the larger peak amplitude in the difference signal; comparing the number of reversal points to a corresponding number of reversal points (NRP) threshold; and determining whether or not to classify the R-wave as being falsely detected due to T-wave oversensing based on results of the comparing the number of reversal points to the corresponding NRP threshold.

In accordance with certain embodiments, a method also comprises comparing an amount of the detected R-waves, that were initially used to detect the tachycardia and were thereafter classified as being falsely detected due to T-wave oversensing, to a corresponding T-wave oversensing threshold, and rejecting the tachycardia detection in response to the amount of the R-waves classified as being falsely detected due to T-wave oversensing equaling or exceeding the corresponding T-wave oversensing threshold.

In accordance with certain embodiments, a method also comprises marking or classifying a tachycardia detection as potentially being a ventricular tachycardia (VT) when at least two consecutive ones of the detected R-waves are classified as being falsely detected due to T-wave oversensing.

In accordance with certain embodiments, in response to none of the R-waves being classified as being falsely detected due to T-wave oversensing, the method further comprises: determining a signal envelope guided R-wave detection threshold; redetecting R-waves in the difference signal by comparing the amplitude of the difference signal to the signal envelope guided R-wave detection threshold; determining a redetected heart rate (HR) or redetected R-R intervals based on the redetected R-waves; and determining whether or not to reject the tachycardia detection based on the redetected HR or the redetected R-R intervals. In certain such embodiments, wherein the determining whether or not to reject the tachycardia detection based on the redetected HR or the redetected R-R intervals comprises comparing the redetected HR or an average of the redetect R-R intervals to a corresponding threshold indicative of the redetected HR being too slow to be an actual tachycardia, and selectively rejecting the tachycardia detection based on results of the comparing the redetected HR or the average of the redetect R-R intervals to the corresponding threshold indicative of the redetected HR being too slow to be a tachycardia.

In accordance with certain embodiments, the determining the signal envelope guided R-wave detection threshold comprises: extracting a signal envelope from the difference signal by identifying a maximum value of the difference signal within a moving window; determining a coefficient of variation of the signal envelope; identifying a minimum value in the signal envelope; comparing the coefficient of variation of the signal envelope to a corresponding coefficient of variation (COV) threshold; setting the signal envelope guided R-wave detection threshold to a product of a first predetermine value multiplied by the minimum value in the signal envelope, when the coefficient of variation is less than the corresponding COV threshold; and setting the signal envelope guided R-wave detection threshold to a product of a second predetermined value multiplied by the minimum value in the signal envelope, when the coefficient of variation is greater than the corresponding COV threshold, wherein the second predetermined value is greater than the first predetermined value.

In accordance with certain embodiments, in response to none of the R-waves being classified as being falsely detected due to T-wave oversensing, the method further comprises: determining a minimal sensed R-wave amplitude guided threshold; redetecting R-waves in the difference signal by comparing the amplitude of the difference signal to the minimal sensed R-wave amplitude guided threshold; determining a redetected heart rate (HR) or redetected R-R intervals based on the redetected R-waves; and determining whether or not to reject the tachycardia detection based on the redetected HR or the redetected R-R intervals.

In accordance with certain embodiments, the determining whether or not to reject the tachycardia detection based on the redetected HR or the redetected R-R intervals comprises: comparing the redetected HR or an average of the redetect R-R intervals to a corresponding threshold indicative of the redetected HR being too fast to be an actual tachycardia; and selectively rejecting the tachycardia detection based on results of the comparing the redetected HR or the average of the redetect R-R intervals to the corresponding threshold indicative of the redetected HR being too fast to be an actual tachycardia.

In accordance with certain embodiments, the determining the minimal sensed R-wave amplitude guided threshold comprises identifying a smallest R-wave peak in the difference signal, and setting the minimal sensed R-wave amplitude guided threshold to a value that is less than the smallest R-wave peak in the difference signal. In certain such embodiments, when redetecting R-waves in the difference signal, by comparing the amplitude of the difference signal to the minimal sensed R-wave amplitude guided threshold, a length of a refractory period that is used for the redetecting is less than a length of a refractory period that is used to initially detect R-waves when comparing the amplitude of the sensed signal indicative of cardiac electrical activity to the R-wave detection threshold.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIG. 3 is a high level flow diagram used to describe how a tachycardia can be detected based on a difference signal, such as a dEGM signal, at an instance of step 108a in FIG. 1A, in accordance with certain embodiments of the present technology.

FIG. 6 is a flow diagram that is used to describe additional details of how an envelope guides R-wave detection threshold can be set at an instance of step 448 in FIG. 4B, in accordance with certain embodiments of the present technology.

DETAILED DESCRIPTION

Figure 1A:
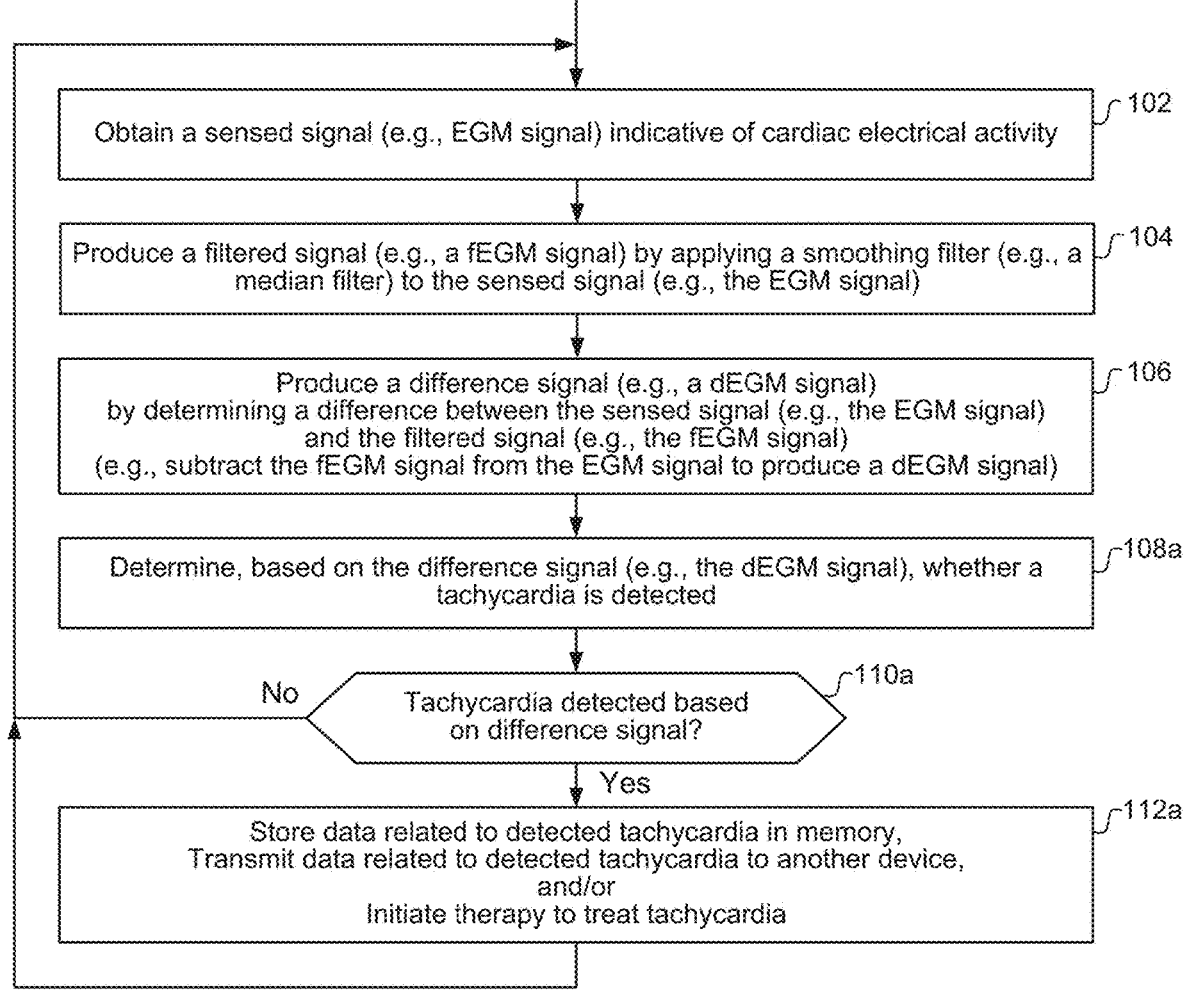
FIG. 1A is a high level flow diagram used to describe certain embodiments of the present technology that can be used to improve detections of tachycardias.

It is well known that each cardiac cycle represented within an electrogram (EGM) or electrocardiogram (ECG) typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of cardiac electrical activity of a patient's heart.

The R-wave is typically the largest wave in the QRS complex, and is often identified by comparing samples of an EGM or ECG to an R-wave detection threshold. Various measurements can be obtained based on the EGM or ECG waveform, including measurements of R-R intervals, where an R-R interval is the duration between a pair of consecutive R-waves. R-waves and R-R intervals are examples of characteristics of an EGM or ECG signal, or more generally, of a signal indicative of cardiac electrical activity of a patient's heart. A patient's heart rate (HR) can be determined, for example, based on measured R-R intervals, as is known art.

IMDs often use algorithms to detect an arrythmia, such as a ventricular tachycardia (VT), wherein such algorithms are often based on the detection of R-waves and R-R intervals, or more generally, based on one or more characteristics of a signal indicative of electrical activity of a patient's heart. For an example, certain such algorithms are trained with VT and non-VT data. Then, after the algorithm has been trained, the algorithm is used at each beat to analyze a prior predetermine number of beats (e.g., the prior 64 beats) and based thereon classify a patient's cardiac rhythm as VT or non-VT.

When monitoring for an arrythmia based on one or more characteristics (e.g., R-waves, R-R intervals, or peak-to-peak intervals) of a signal indicative of cardiac electrical activity, it is possible that certain characteristics, such as R-waves and/or R-R intervals, are inaccurately identified, which can lead to false positive arrhythmia detections. Such false positive arrythmia detections can be due, for example, to T-wave oversensing, which can occur when T-waves having relatively large amplitudes are mistakenly detected as R-waves. More specifically, where a T-wave is mistakenly detected as an R-wave, it can be said that T-wave oversensing occurred, or that an over-sensed R-wave was detected. Where T-wave oversensing occurs, a true R-R interval may be bisected into two shorter intervals, the sum of which is the true R-R interval. Accordingly, T-wave oversensing may lead to a tachycardia, such as a ventricular tachycardia (VT) or atrial fibrillation (AF), being mistakenly detected. Noise artifacts, which are mistakenly identified as R-waves, may also lead to false tachycardia detections.

Figure 1B:
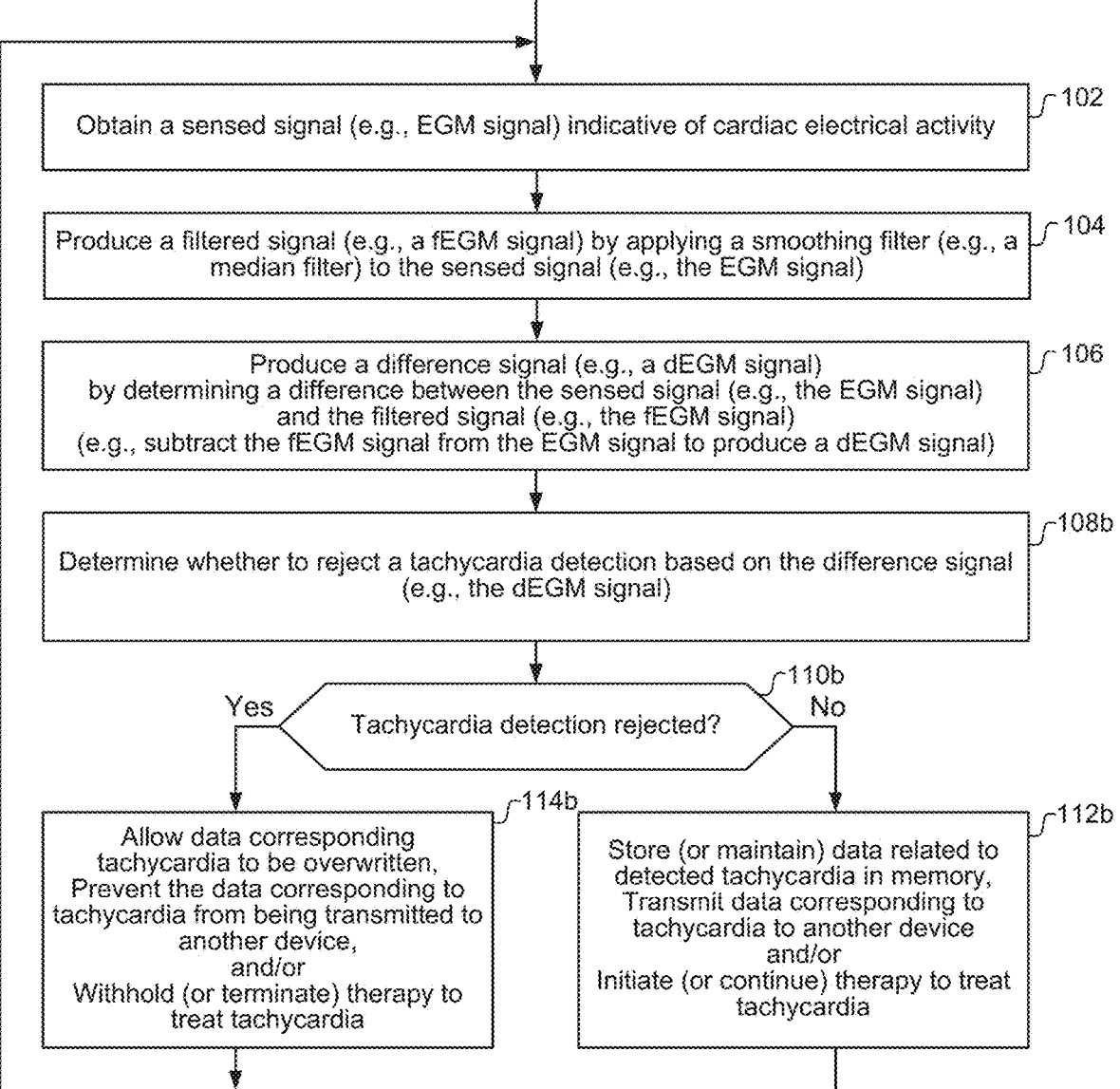
FIG. 1B is a high level flow diagram used to describe certain embodiments of the present technology that can be used to reject false positive detections of tachycardias.

Certain embodiments of the present technology, which are initially disclosed with reference to the high level flow diagrams of FIGS. 1A and 1B, relate to producing a difference signal indicative of cardiac electrical activity, and detecting a tachycardia based on the difference signal or determining whether or not to reject a tachycardia detection based on the difference signal. A benefit of using the difference signal, rather than an originally sensed signal indicative of cardiac electrical activity (e.g., an EGM or an ECG signal), is that T-wave amplitudes in the difference signal will typically be much smaller than T-wave amplitudes in the originally sensed signal, which should lead to less T-wave oversensing.

Referring to FIG. 1A, step 102 involves obtaining a sensed signal indicative of cardiac electrical activity. Such a sensed signal can be, for example, an EGM signal or an ECG signal. For much of the remaining discussion, the signal obtained at step 102 is presumed to be an EGM, unless stated otherwise. The signal obtained at step 102 can be obtained, for example, using two or more electrodes and a sensing circuit that is coupled to the two or more electrodes, as is well known in the art. It is also possible that the signal obtained at step 102 is sensed and stored in a buffer or memory for later analysis, in which case obtaining the sensed signal can involve retrieving, uploading, or otherwise receiving the sensed signal from the buffer or memory.

Still referring to FIG. 1A, step 104 involves producing a filtered signal indicative of cardiac electrical activity by applying a smoothing filter to the sensed signal indicative of cardiac electrical activity. In accordance with certain embodiments, the smoothing filter used at step 104 is a median filter, in which case step 104 involves producing the filtered signal indicative of cardiac electrical activity by applying a median filter to the sensed signal indicative of cardiac electrical activity. Applying a median filter involves processing a digital version of a signal, one digital value at a time, by replacing each digital value with the median of neighboring data values. The pattern of neighbors is called the "window", which slides, data value by data value, over the entire signal. For an example, the window, which can also be referred to as the filter length, can include a total of twenty data values, including the ten preceding data values and the ten following data values. For another example, the window, which can also be referred to as the filter length, can be temporally defined, e.g., can be 120 milliseconds (msec) in length, which includes the 60 msec preceding a data value and the 60 msec following the data value. Other variations are also possible and within the scope of the embodiments described herein. It would also be possible to use other types of smoothing filters, besides a median filter. For example, a weighted moving average filter, a Lulu smoothing filter, or a bilateral filter can be used at step 104 to produce the filtered signal indicative of cardiac electrical activity. Where the signal sensed at step 102 is an EGM, the signal produced at step 104 can be referred to as a filtered EGM signal, or more succinctly as an fEGM signal. It is noted that there can be some pre-filtering performed between steps 102 and 104, and/or that the signal obtained at step 102 is already pre-filtered. Such pre-filtering can be performed, e.g., using a low pass filter, a high pass filter, or a bandpass filter.

Still referring to FIG. 1A, step 106 involves producing a difference signal indicative of cardiac electrical activity by determining a difference between the sensed signal indicative of cardiac electrical activity, which was obtained at step 102, and the filtered signal indicative of cardiac electrical activity, which was produced at step 104. Where the signal sensed at step 102 is an EGM signal, the difference signal can be referred to as a difference EGM signal, or more succinctly as a dEGM signal, or alternatively as a delta EGM signal or a AEGM signal. The difference signal can be produced at step by subtracting the filtered signal (e.g., the fEGM signal) produced at step 104 from the sensed signal (e.g., the EGM signal) obtained at step 102. Alternatively, the difference signal can be produced by subtracting the sensed signal (e.g., the EGM signal) obtained at step 102 from the filtered signal (e.g., the fEGM signal) produced at step 104, and rectifying or flipping the polarity of the result, to thereby produce the difference signal. For the remainder of this discussion, unless stated otherwise, it is assumed that the difference signal is obtained by subtracting an fEGM signal produced at step 104 from an EGM signal obtained at step 102. In certain embodiments, the difference signal is rectified before being used at step 108a, discussed below, wherein rectifying the difference signal involves converting negative values to positive values.

Step 108a involves detecting a tachycardia based on the difference signal. In other words, the difference signal can be analyzed to detect a tachycardia in the first place. More generally, at step 108a there is a determination, based on the difference signal (e.g., dEGM), of whether a tachycardia is detected. For example, step 108a can involve using the difference signal (e.g., dEGM signal) to detect R-waves, R-R intervals, and/or the like, and based thereon, detecting a tachycardia, such as VT, but not limited thereto. This is in contrast to just using the sensed signal (e.g., EGM signal), or a filtered version thereof, to detect R-waves, R-R intervals, and/or the like, and based thereon, detecting a tachycardia. Additional details of step 108a, according to specific embodiments of the present technology, are described below with reference to FIG. 3. Alternatively, any known or future developed techniques for detecting VT or another type of tachycardia based on R-wave, R-R intervals, and/or the like, can be used. In other words, the improvement provided by embodiments of the present technology described herein with reference to FIG. 1A are not necessarily limited to the tachycardia detection algorithm itself. Rather, the improvement is achieved, at least in part, by the tachycardia detection being based on the difference signal that is produced at step 106, by determining a difference between the sensed signal (obtained at step 102) and the filtered signal (produced at step 104).

Still referring to FIG. 1A, at step 110a there is a determination of whether a tachycardia was detected. While steps 108b and 110b are shown as separate steps in FIG. 1B, those steps can equivalently be combined into a single step. If the answer to the determination at step 110a is No, then flow returns to step 102. If the answer to the determination at step 110a is Yes, then flow goes to step 112a. At step 112a data related to the detected tachycardia is stored in memory so that it is available for further analysis. Alternatively, or additionally, at step 112a data related to the detected tachycardia is transmitted to another device, which other device can be an implanted device or a non-implanted device, such as, but not limited to, an external monitor or an external programmer. Alternatively, or additionally, if the method described with reference to FIG. 1A is performed by an implantable device that is capable of performing therapy, such as anti-tachycardia pacing (ATP), to treat the tachycardia (e.g., convert the tachycardia to a normal sinus rhythm), then such therapy can be initiated at step 112a.

FIG. 1B will now be used to describe embodiments of the present technology that utilize the difference signal, produced at step 106, to determine whether or not to reject a tachycardia detection. Referring to FIG. 1B, steps 102, 104 and 106 in FIG. 1B are the same as those similarly numbered steps described above with reference to FIG. 1A, and thus, these steps need not be described again in detail. Still referring to FIG. 1B, at step 108a the difference signal is used to determine whether or not to reject a tachycardia detection. In certain embodiments, the difference signal is rectified before being used at step 108b, discussed below, wherein rectifying the difference signal involves converting negative values to positive values, as noted above. Regardless of whether or not the difference signal is rectified before being used at step 108b, it can still be said that step 108b involves determining whether or not to reject a tachycardiac detection based on the difference signal. Example details of step 108b, according to certain embodiments of the present technology, are described below with reference to FIGS. 4A-4C. In accordance with certain embodiments, where the different signal is used to determine whether or not to a reject a tachycardia detection, the sensed signal that is obtained at step 102, filtered at step 104, and used to produce the difference signal at step 106, can be a stored segment of the sensed signal that was used to detect the tachycardia in the first place.

Still referring to FIG. 1B, at step 110b there is a determination of whether the tachycardia detection was rejected. While steps 108b and 110b are shown as separate steps in FIG. 1B, those steps can equivalently be combined into a single step. If the answer to the determination at step 110b is Yes, then flow goes to step 112b. At step 112b data related to the detected tachycardia is stored in memory (or maintained in memory, e.g., by not being overwritten, if already stored) so that it is available at a later time for further analysis, and/or available for upload to another device or system. Alternatively, or additionally, at step 112a data related to the detected tachycardia is transmitted to another device, which other device can be an implanted device or a non-implanted device or system, such as, but not limited to, an external monitor or an external programmer. Alternatively, or additionally, if the method described with reference to FIG. 1A is performed by an implantable device that is capable of performing therapy, such as anti-tachycardia pacing (ATP), to treat the tachycardia (e.g., convert the tachycardia to a normal sinus rhythm), then such therapy can be initiated at step 112a (or if already initiated, can be continued).

In summary, the difference signal produced at an instance of step 106 can be analyzed to detect a tachycardia in the first place, as described above with reference to FIG. 1A. Alternatively, as described above with reference to FIG. 1B, in certain embodiments the difference signal may be produced after a tachycardia has been detected based on the signal obtained at step 102, and then the difference signal is used to determine whether the tachycardia detection was likely falsely detected, and thus, should be rejected.

Figure 2:
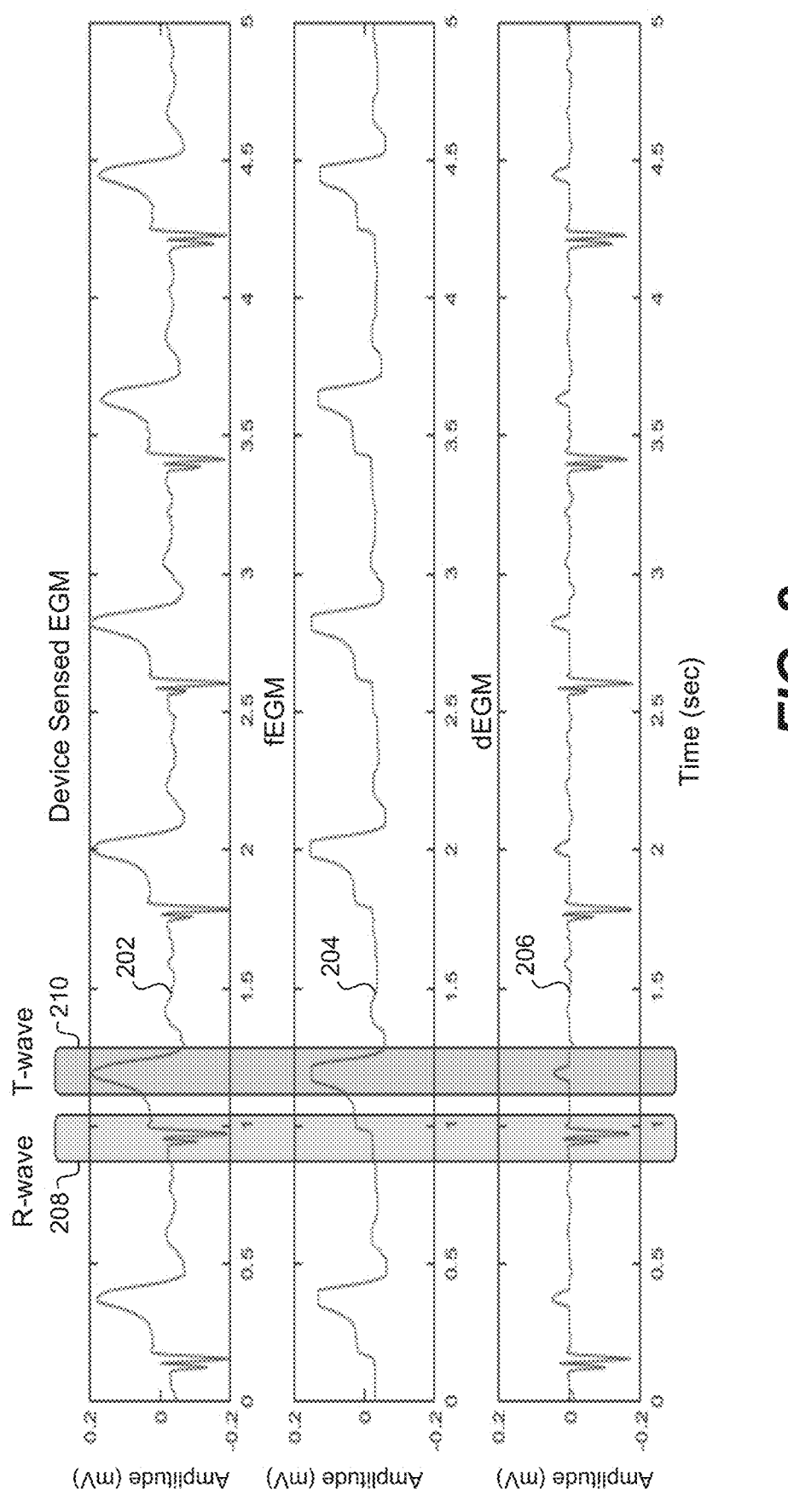
FIG. 2 shows in the top panel an example of a sensed EGM signal that can be obtained at an instance of step 102 in FIGS. 1A and 1B, shows in the middle panel an example of a filtered EGM (fEGM) signal that can be produced at an instance of step 104 in FIGS. 1A and 1B, and shows in the bottom panel an example of a difference EGM (dEGM) signal that can be produced at an instance of step 106 in FIGS. 1A and 1B.

Referring now to FIG. 2, the top panel shows an example of a sensed EGM signal 202 obtained at step 102, the middle panel shows an example of an fEGM signal 204 produced at step 104, and the bottom panel shows an example of a dEGM signal 206 produced at step 106. The vertically elongated rectangle 208 in FIG. 2 includes portions of the signals 202, 204, 206 that correspond to an R-wave, and the vertically elongated rectangle 210 includes portions of the signals 202, 204, 206 that correspond to a T-wave.

As can be appreciated from the EGM signal 202 shown in the top panel in FIG. 2, the magnitude of the peak amplitude of the T-wave within the rectangle 210 is similar to the magnitude of the peak amplitude of the R-wave within the rectangle 208, which would likely lead to T-wave oversensing. As can be appreciated from the fEGM signal 204 shown in the middle panel in FIG. 2, the R-waves are primarily filtered out, leaving primarily just T-waves, such that after the fEGM signal 204 is subtracted from the EGM signal 202 to produce the dEGM signal 206, the magnitude of the T-waves are much smaller than the magnitudes of the R-waves, thereby reducing the probability of T-waves being falsely detected as R-waves in the dEGM signal.

The high level flow diagram of FIG. 3 will now be used to describe how a tachycardia can be detected based on a dEGM, or more generally, based on a difference signal produced at step 108. In other words, the high level flow diagram of FIG. 3 is used to describe how a tachycardia can be detected based on the difference signal at an instance of step 108, introduced above in the discussion of FIG. 1.

Referring to FIG. 3, for completeness, steps 102, 104 and 106, which were introduced above with reference to FIG. 1A are shown, but need not be described again. Step 310 involves comparing an amplitude of the difference signal to an R-wave detection threshold, and step 312 involves detecting R-waves based on results of the comparing. In other words, at step 310 and 312 collectively, the amplitude of the difference signal (e.g., the dEGM signal) is compared to an R-wave detection threshold to thereby detect R-waves in the difference signal. Such an R-wave detection threshold may be a constant threshold or a dynamic threshold. Where the R-wave detection threshold is dynamic, it may nominally be at a programmed maximum sensitivity level. Once the R-wave detection threshold is reached or exceeded, which results in an R-wave detection, that starts a sense refractory period, during which the sensed signal is not compared to the dynamic sensing threshold, and during which a peak of the sensed signal within the sense refractory period is identified, wherein the peak is the peak R-wave amplitude. At the end of the sense refractory period, the dynamic sensing threshold is set to a programmed percentage (e.g., 62.5%) of the peak R-wave amplitude. For an example, if the peak R-wave amplitude is 7 millivolts (mV), then the dynamic sensing threshold will be set to 3.75 mV at the end of the sense refractory period. The dynamic sensing threshold remains at that amplitude (i.e., at 3.75 mV in this example) for a programmed decay delay (e.g., 60 milliseconds (msec)) before beginning to decay at a programmed decay rate (e.g., 1 mV per second) until reaching the maximum sensitivity level. The maximum sensitivity level can be the same as the minimum magnitude of the dynamic sensing threshold, but that need not be the case. This is just one example of how a dynamic R-wave detection threshold can be provided. Other variations are also possible and within the scope of the embodiments described herein. While steps 310 and 312 are shown as two separate steps, these steps can be combined into a single step, as would be appreciated by one of skill in the art reviewing the flow diagram of FIG. 3. It is noted that whenever a signal (e.g., a dEGM signal) is described herein as being compared to a threshold, this can be achieved by comparing a sample of the signal (e.g., the dEGM signal) to the threshold. Similarly, it is noted that whenever a signal (e.g., an EGM signal) is described herein as being filtered, this can be achieved in the digital domain by applying a filter to the samples of the signal (e.g., samples of the EGM), wherein such samples are digital values.

Step 314 involves determining a heart rate (HR) and/or R-R intervals based on the detected R-waves. In certain embodiments, an R-R interval is determined for each detected R-wave, by determining an interval between each detected R-wave and the immediately preceding detected R-wave. In certain such embodiments, each R-wave is tagged or otherwise classified as a tachycardia beat if the R-R interval determined for the R-wave is less than a corresponding R-R interval tachycardia threshold, which can be set by default or programmed by a physician. An example R-R interval tachycardia threshold is 500 msec, which corresponds to an HR of at least 120 beats per minute (bpm), but is not limited thereto.

In certain embodiments, a tachycardia can be detected at step 316 using a tachycardia counter that is initiated in response to an R-wave being classified as a tachycardia beat, and the tachycardia counter is incremented when the next R-wave is classified as a tachycardia beat or remains the same value if the next R-wave is not classified as a tachycardia beat. Once the tachycardia counter reaches a programmed threshold (e.g., nominally equal to 12, or programmed to a different value by a clinician), a tachycardia episode is detected. The counter is reset back to zero when a specified number of consecutive sinus beats are sensed (e.g. four consecutive sinus beats). So if four consecutive sinus beats are sensed before the counter reaches its programmed threshold (e.g., 12), a tachycardia episode is not detected. When an R-wave is classified as a tachycardia beat it can equivalently be said that the R-wave is within a tachycardia zone.

In other embodiments, a tachycardia is detected by determining a moving average of R-R intervals, comparing the moving average to a corresponding R-R interval tachycardia threshold, and detecting a tachycardia when the moving average is less than the threshold, or is less than the threshold for at least a specified number of beats or for at least a specified amount of time. Alternatively, the moving average of the R-R intervals can be converted to a moving average HR, and a tachycardia can be detected when the moving average HR exceeds a corresponding HR threshold (e.g., 120 bpm), or when the moving average HR exceeds the corresponding HR threshold for at least a specified number of beats or at least a specified amount of time. Other variations are also possible, and within the scope of the embodiments described herein.

Referring briefly back to step 108*b* in FIG. 1B, as was noted above, in certain embodiments the difference signal is produced at an instance of step 106 after a tachycardia has been detected based on the signal obtained at step 102, and then the difference signal is used to determine whether the tachycardia detection was likely falsely detected, and thus, should be rejected. As was also noted above, the difference signal can be rectified before being used at step 108, wherein rectifying the difference signal involves converting negative values to positive values. Regardless of whether or not the difference signal is rectified before being used at step 108, it can still be said that step 108 involves detecting a tachycardia based on the difference signal, or determining whether or not to reject a tachycardia detection based on the difference signal.

Figure 4A:
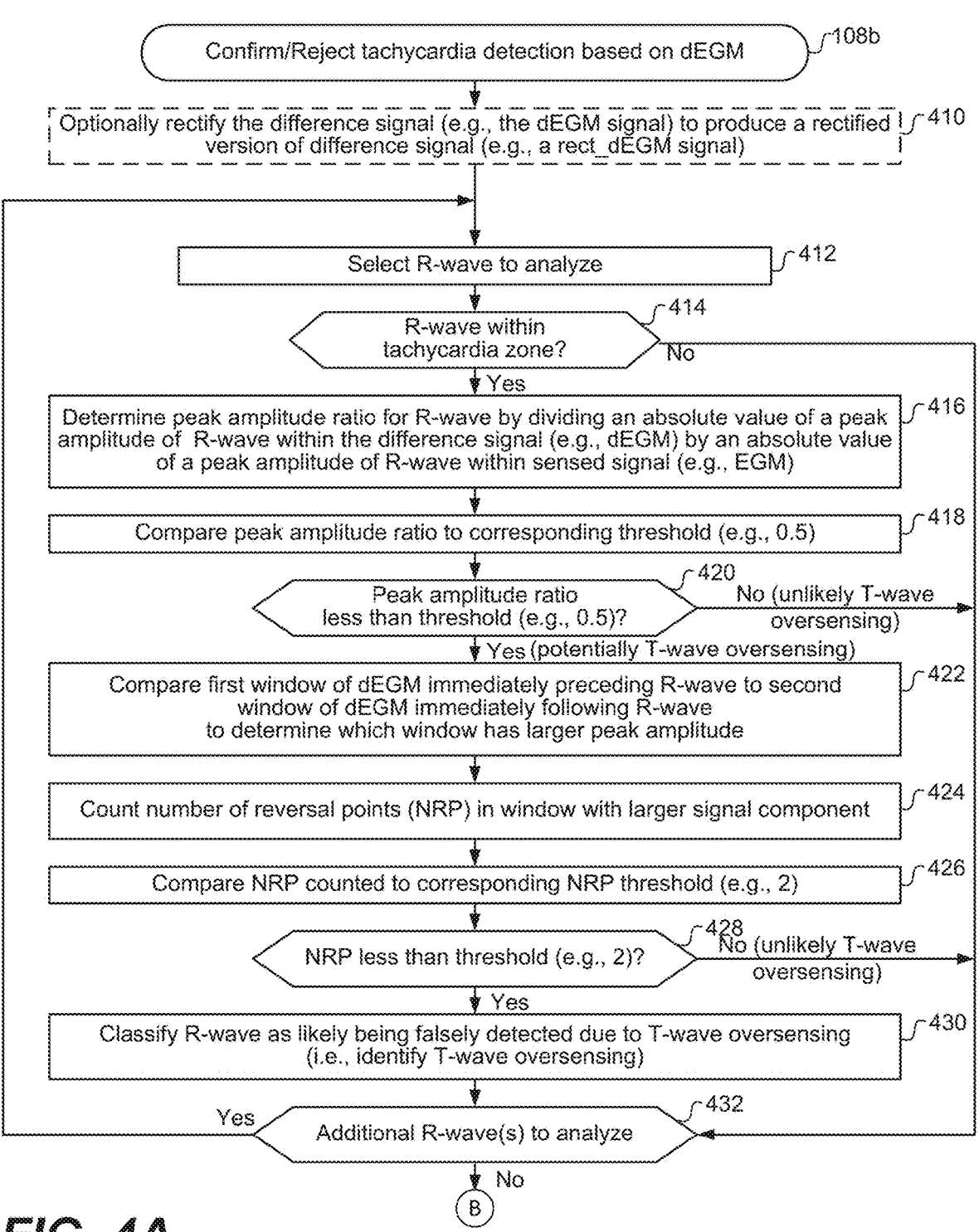
FIGS. 4A, 4B and 4C, which can be collectively referred to as FIG. 4, show a high level flow diagram used to describe how there can be a determination of whether or not to reject a detected tachycardia based on a difference signal (e.g., a dEGM signal), at an instance of step 108b in FIG. 1B, in accordance with certain embodiments of the present technology.
Figure 4B:
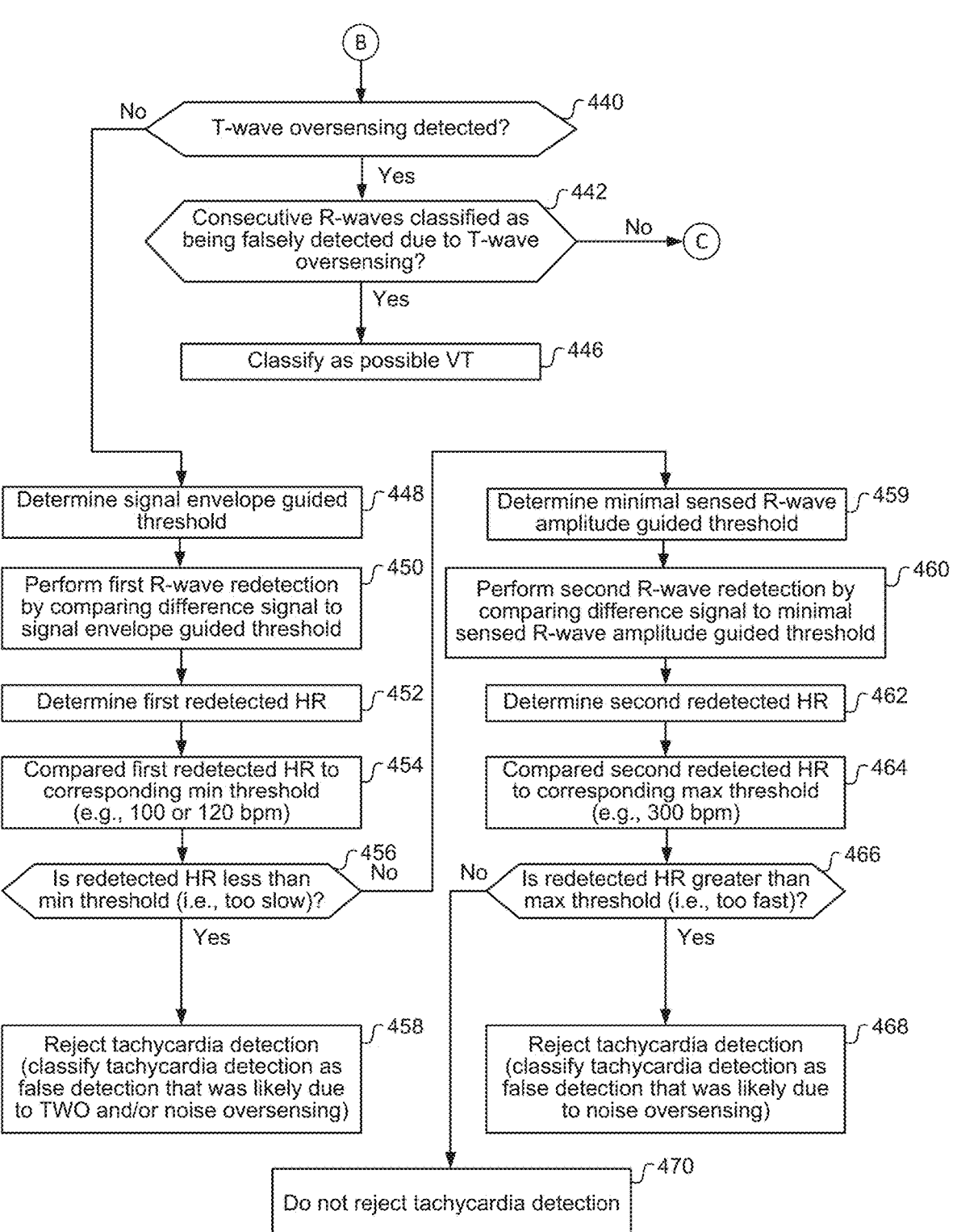
Figure 4C:
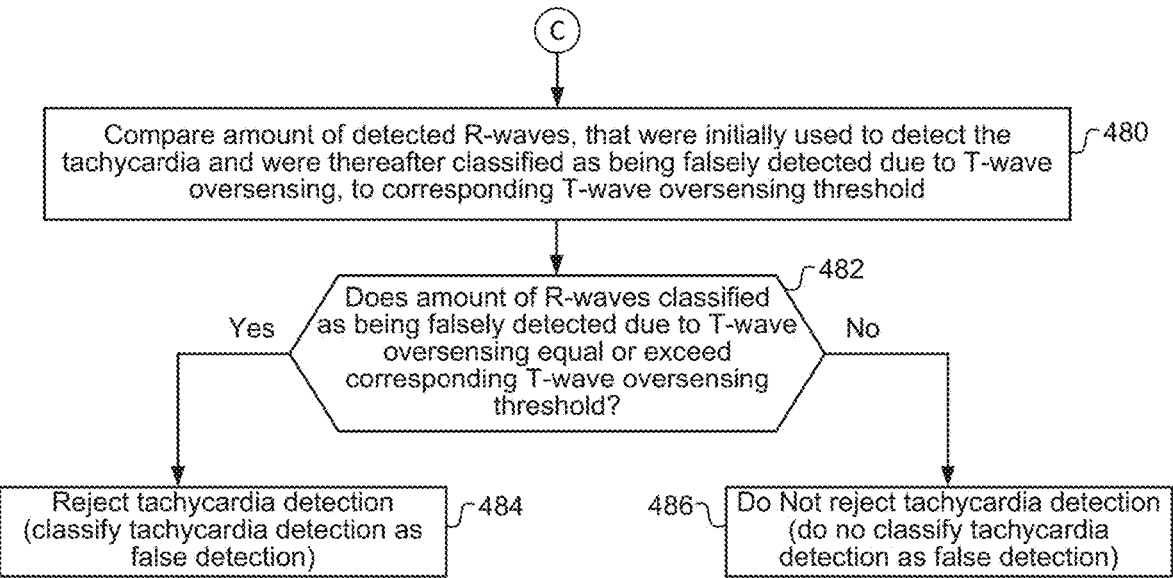

The high level flow diagram of FIGS. 4A, 4B and 4C (which can be collectively referred to as FIG. 4) is now used to describe how, in accordance with certain embodiments, there can be a determination based on the difference signal (e.g., a dEGM signal) of whether or not to reject a detected tachycardia. Referring to FIG. 4A, the difference signal can be rectified at an optional step 410, which is shown in dashed line. Still referring to FIG. 4A, step 412 involves selecting an R-wave to analyze from a window (e.g., a window having a specified length of time, or a window including a specified number of R-waves, but not limited thereto) leading up to a tachycardia detection, and step 414 involves determining whether the selected R-wave has been determined to be within the tachycardia zone (i.e., was classified as being a tachycardia beat). If the answer to the determination at step 414 is No (i.e., if the selected R-wave was not classified as being a tachycardia beat), then flow goes to step 432, as shown. At step 432 there is a determination of whether there is/are any additional R-wave(s) to analyze. If the answer to the determination at step 432 is Yes, then flow returns to step 412, at which another R-wave is selected to analyze. If the answer to the determination at step 432 is No, then flow goes to step 440 in FIG. 4B, which is discussed below.

Returning to step 414, if the answer to the determination at step 414 is Yes (i.e., if the R-wave was classified as being a tachycardia beat), then flow goes to step 416. Step 416 involves determining a peak amplitude ratio for the detected R-wave by dividing a peak amplitude of the R-wave within the difference signal by a peak amplitude of the detected R-wave within the sensed signal, and step 418 involves comparing the peak amplitude ratio to a corresponding peak amplitude ratio (PAR) threshold. The PAR threshold can be in the range of 0.4 to 0.6 (e.g., 0.5), but is not limited thereto. Step 420 involves determining whether the peak amplitude ratio (determined at step 416) is less than the corresponding PAR threshold. If the answer to the determination at step 420 is No, then it is unlikely that the R-wave being analyzed was detected due to T-wave oversensing, and flow goes to step 432. If the answer to the determination at step 420 is Yes, then the R-wave may have been detected due to T-wave oversensing, and flow goes to step 422 so that additional analysis is performed to determine whether or not the R-wave was likely detected due to T-wave oversensing. While steps 418 and 420 are shown as two separate steps in FIG. 4A, they can be combined into a single step, as would be appreciated by one of skill in the art reviewing the flow diagram.

Step 422 involves comparing a first window of the difference signal immediately preceding the detected R-wave to a second window of the difference signal immediately following the detected R-wave to thereby determine which one of the first and the second windows has a larger peak amplitude. Step 424 then involves counting a number of reversal points in the one of the first and the second windows of the difference signal that has the larger peak amplitude in the difference signal. An example of this will be described below with reference to FIG. 5. Still referring to FIG. 4A, step 426 involves comparing the number of reversal points (counted at step 424) to a corresponding number of reversal points (NRP) threshold (e.g., the NRP threshold equals 2, but is not limited thereto). Step 426 involves determining whether the number of reversal points (counted at step 424) is less than the corresponding NRP threshold (e.g., 2). If the answer to the determination at step 428 is No, then the R-wave was unlikely detected due to T-wave oversensing, and flow goes to step 432. In other words, if the answer to step 428 is No, then the R-wave being analyzed is likely a true R-wave. If the answer to the determination at step 428 is Yes, then flow goes to step 430 and the R-wave is classified as likely being detected due to T-wave oversensing. In other words, at step 430 the R-wave being analyzed is classified as an over-sensed T-wave. More generally, steps 424, 426, 428 and 430 involve determining whether or not to classify an R-wave detection as being falsely detected due to T-wave oversensing based on results of comparing the number of reversal points to the corresponding NRP threshold. After step 430, flow then goes to step 432. So long as the answer to step 432 is Yes, flow returns to step 412. When the answer to step 422 is No, then flow goes to step 440 in FIG. 4B. Steps 414 and 420 in FIG. 4A are performed to reduce computations, and more specifically, so that the steps 422 through 428 are only performed for R-wave detections that possibly resulted from T-wave oversensing.

Referring now to FIG. 4B, at step 440 there is a determination of whether any of the R-waves were classified as being falsely detected due to T-wave oversensing. In other words, step 440 involves determining whether T-wave oversensing was detected during the analysis of the R-waves that were analyzed during the steps described above with reference to FIG. 4A. If the answer to the determination at step 440 is No (i.e., if T-wave oversensing was not detected), then flow goes to step 448. If the answer to the determination at step 440 is Yes (i.e., if T-wave oversensing was detected), then flow goes to step 442.

At step 442 that is a determination of whether consecutive R-waves were classified as being falsely detected due to T-wave oversensing. If the answer to the determination at step 442 is No, then flow goes to step 480 in FIG. 4C, discussed below. If the answer to the determination at step 442 is Yes, then flow goes to step 446 and the tachycardia is classified as being a possible ventricular tachycardia (VT). In other words, if two or more consecutive R-waves are classified as falsely being detected due to T-wave oversensing, then the tachycardiac detection is likely to be a true VT instead of T-wave oversensing. Such classification information can be stored in memory of a device, along with an EGM segment corresponding to the tachycardia. If the IMD is capable of performing therapy, the VT detection can be used to trigger an appropriate therapy.

Returning to step 440, if none of the R-waves analyzed in response to a tachycardia detection is classified as being a false detection due to T-wave oversensing, then flow goes to step 448, as noted above. At step 448 a signal envelope guided threshold is determined, and step 450 involves performing R-wave redetections by comparing the amplitude of the difference signal (e.g., a dEGM signal) to the signal envelope guided threshold determined at step 448. An example of how to determine the signal envelope guided threshold, at step 448, is described below with reference to the high level flow diagram of FIG. 6 and the example dEGM signals shown in FIG. 7. In accordance with certain embodiments, when the R-wave redetections are performed at step 450 by comparing the amplitude of the difference signal (e.g., the dEGM signal produced at an instance of step 106) to the signal envelope guided threshold (produced at an instance of step 448), a shortened refractory period is used (e.g., of 150 msec, but not limited thereto) that is shorter than the refractory period that was used when making the original R-wave detections, e.g., at instances of steps 310 and 312.

Still referring to FIG. 4B, step 452 involves determining a first redetected heart rate (HR) based on the first redetected R-waves detected at step 450, and step 454 involves comparing the first redetected HR to a corresponding minimum threshold (e.g., 100 bpm, or 120 bpm, but not limited thereto) that is indicative of the first redetect HR being too slow to be an actual tachycardia. At step 456 there is a determination of whether the first redetected HR is less than a corresponding minimum threshold that is indicative of the first redetect HR being too slow to be an actual tachycardia. If the answer to the determination at step 456 is Yes, then flow goes to step 458, and the tachycardia detection is rejected. Explained another way, at step 458 the tachycardia detection is classified as being a false detection that was likely due to T-wave oversensing and/or noise oversensing. While steps 454 and 456 are shown as two separate steps, they can be combined into a single step, as would be appreciated by one of skill in the art reviewing the flow diagram.

Still referring to FIG. 4B, if the answer to the determination at step 456 is No, then flow goes to step 459. Step 459 involves determining a minimal sensed R-wave amplitude guided threshold. In certain embodiments, the minimal sensed R-wave amplitude guided threshold is determined by identifying a smallest R-wave peak in the difference signal (e.g., the dEGM signal), and setting the minimal sensed R-wave amplitude guided threshold to a value that is less than the smallest R-wave peak in the difference signal. For example, the minimal sensed R-wave amplitude guided threshold can be set to a value that is 10% (or some other percent) less than the smallest R-wave peak in the difference signal. Equivalently, the minimal sensed R-wave amplitude guided threshold can be set to a value that is 90% (or some other percent) of the smallest R-wave peak in the difference signal. Other variations are also possible and within the scope of the embodiments described herein. Step 460 involves performing a second redetecting of R-waves in the difference signal by comparing the amplitude of the difference signal to the minimal sensed R-wave amplitude guided threshold. Step 462 involves determining a second redetected heart rate (HR) based on the second redetected R-waves detected at step 460, and step 464 involves comparing the second redetected HR to a corresponding maximum threshold (e.g., 300 bpm, or 320 bpm, but not limited thereto) that is indicative of the second redetect HR being too fast to be an actual tachycardia. At step 466 there is a determination of whether the second redetected HR is greater than the corresponding maximum threshold that is indicative of the second redetect HR being too fast to be an actual tachycardia. If the answer to the determination at step 466 is Yes, then flow goes to step 468, and the tachycardia detection is rejected. Explained another way, at step 468 the tachycardia detection is classified as being a false detection that was likely due to noise oversensing. If the answer to the determination at step 466 is No, then flow goes to step 470 and the tachycardia is not rejected (i.e., is not classified as being a false tachycardia detection). While steps 464 and 466 are shown as two separate steps, they can be combined into a single step, as would be appreciated by one of skill in the art reviewing the flow diagram.

In accordance with certain embodiments, when the R-wave redetections are performed at step 460 by comparing the amplitude of the difference signal (e.g., the dEGM signal produced at an instance of step 106) to the minimal sensed R-wave amplitude guided threshold (produced at an instance of step 459), a very short refractory period (e.g., of 100 msec, but not limited thereto) is used that is substantially shorter than the refractory period that was used when making the original R-wave detections, e.g., at instances of steps 310 and 312, and is also shorter than the shortened refractory period used at step 450.

In certain alternative embodiments, when the answer to the determination at step 440 is No, flow can go directly to step 459. Then, if the answer to the determination at step 466 is No, flow goes to step 448. Then, if the answer to the determination at step 456 is No, flow goes to step 470. In other words, steps 459 through 466 can be performed prior to steps 448 through 456. It would also be possible for steps 459 through 466 to be performed in parallel with steps 448 through 456. Other variations are also possible and within the scope of the embodiments described herein.

Returning to step 442, if the answer to the determination at step 442 is No (i.e., if only non-consecutive R-waves are classified as being falsely detected due to T-wave oversensing), then flow goes to step 480 in FIG. 4C, as was noted above. Referring now to FIG. 4C, at step 480 an amount of the detected R-waves, that were initially used to detect the tachycardia and were thereafter classified as being falsely detected due to T-wave oversensing, is compared to a corresponding T-wave oversensing threshold. At step 482 there is a determination of whether the amount of the detected R-waves, that were initially used to detect the tachycardia and were thereafter classified as being falsely detected due to T-wave oversensing, is equal to or greater than the corresponding T-wave oversensing threshold. If the answer to the determination at step 482 is Yes, then flow goes to step 484, and the tachycardia detection is rejected, i.e., classified as being a false detection. If the answer to the determination at step 482 is No, then flow goes to step 486, and the tachycardia detection is not rejected. The amount of the detected R-waves, and the corresponding T-wave oversensing threshold used at step 480 and 482, can be in terms of a number or a percentage, for example. A tachycardia detection will be rejected if a great enough number or percentage of R-waves in the tachycardia zone are classified as being falsely detected due to T-wave oversensing. For example, assume that a tachycardia detection occurs when at least 12 tachycardia beats are detected before 4 normal sinus rhythm beats are detected. In certain embodiments, if 3 out of 12 (25%) of these tachycardia beats are identified as resulting from T-wave oversensing, then the tachycardia detection is rejected at step 484. While steps 480 and 482 are shown as two separate steps, one of skill in the art would appreciate that these steps can be combined into a single step.

Figure 5:
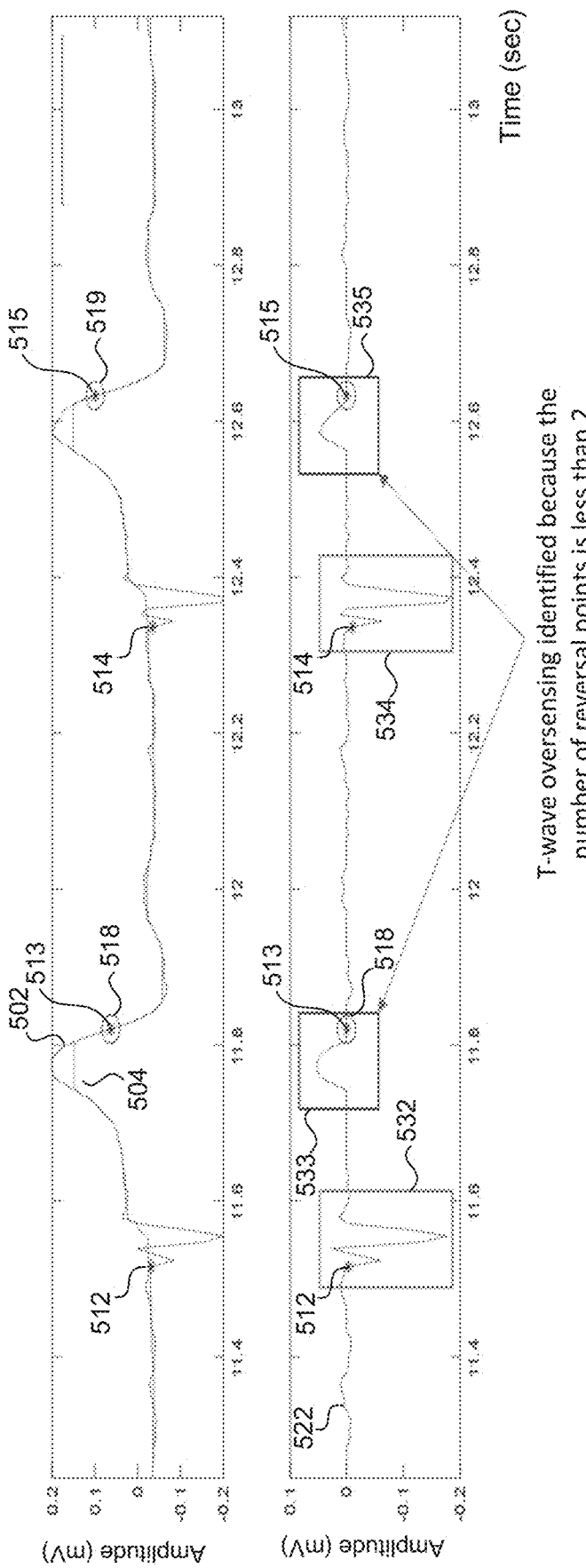
FIG. 5 is used to explain how, at an instance of step 424 in FIG. 4A, the number of reversal points in windows of a difference signal can be counted and used to determine whether or not to classify an R-wave detection as being falsely detected due to T-wave oversensing, in accordance with certain embodiments of the present technology.

FIG. 5 will now be used to explain how, at an instance of step 424 discussed above with reference to FIG. 4A, a number of reversal points can be counted in the one of the first and the second windows of the difference signal that has the larger peak amplitude in the difference signal. The upper panel in FIG. 5 shows a sensed EGM signal 502, a fEGM signal 504, and four R-wave markers 512, 513, 514, and 515 (aka detected R-waves, or R-wave detections), which are illustrated as stars or asterisks. The two R-wave markers 513 and 515 that are surrounded by circles 518 and 519 illustrate R-wave detections that were thereafter classified as being false R-wave detections due to T-wave oversensing, using an embodiment of the present technology.

The lower panel in FIG. 5 shows a dEGM signal 522 produced by subtracting the fEGM 504 from the sensed EGM 502 in the upper panel. In the lower panel, the block labeled 532 generally corresponds to a second window of the dEGM signal 522 immediately following the detected R-wave 512, which has a greater peak amplitude than a first window of the dEGM signal 522 immediately preceding the detected R-wave 512. The block labeled 533 generally corresponds to a first window of the dEGM signal 522 immediately preceding the detected R-wave 513, which has a greater peak amplitude than a second window of the dEGM signal 522 that immediately follows the detected R-wave 513. The block labeled 534 generally corresponds to a second window of the dEGM signal 522 immediately following the detected R-wave 514, which has a greater peak amplitude than a first window of the dEGM signal 522 immediately preceding the detected R-wave 514. The block labeled 535 generally corresponds to a first window of the dEGM signal 522 immediately preceding the detected R-wave 515, which has a greater peak amplitude than a second window of the dEGM signal 522 that immediately follows the detected R-wave 515.

Still referring to FIG. 5, but also briefly referring back to steps 422 through 428 in FIG. 4A, the number of reversal points in the window 532 is 4, the number of reversal points in the window 533 is 1, the number of the reversal points in the window 534 is 4, and the number of reversal points in the window 535 is 1. Assuming the corresponding NRP threshold is equal to 2, then it could be determined that the number of reversal points in the window 532 is greater than the corresponding NRP threshold, and thus, it is unlikely that the R-wave detection 512 was falsely detected due to T-wave oversensing. Looking at the window 533, it can be determined that the number of reversal points in the window 533 is 1, which is less than the corresponding NRP threshold, and thus, the R-wave detection 512 is classified as likely being falsely detected due to T-wave oversensing at an instance of step 430. Looking at the window 534, it can be determined that the number of reversal points in the window 533 is 4, which is greater than the corresponding NRP threshold of 2, and thus, it is unlikely that the R-wave detection 512 was falsely detected due to T-wave oversensing. Looking at the window 535, it can be determined that the number of reversal points in the window 533 is 1, which is indeed less than the corresponding NRP threshold of 2, and thus, the R-wave detection 512 is classified as likely being falsely detected due to T-wave oversensing at an instance of step 430. The rationale behind using the number of reversal points to distinguish true R-waves from R-waves that were mistakenly detected due to T-wave oversensing is that T-waves are typically smoother than R-waves. More specifically, T-waves represented in the difference signal (e.g., the dEGM signal) will rarely have more than one reversal point, wherein a QRS complex (of which an R-wave is a component) represented in the difference signal (e.g., the dEGM signal) will likely have multiple reversal points.

Figure 7:
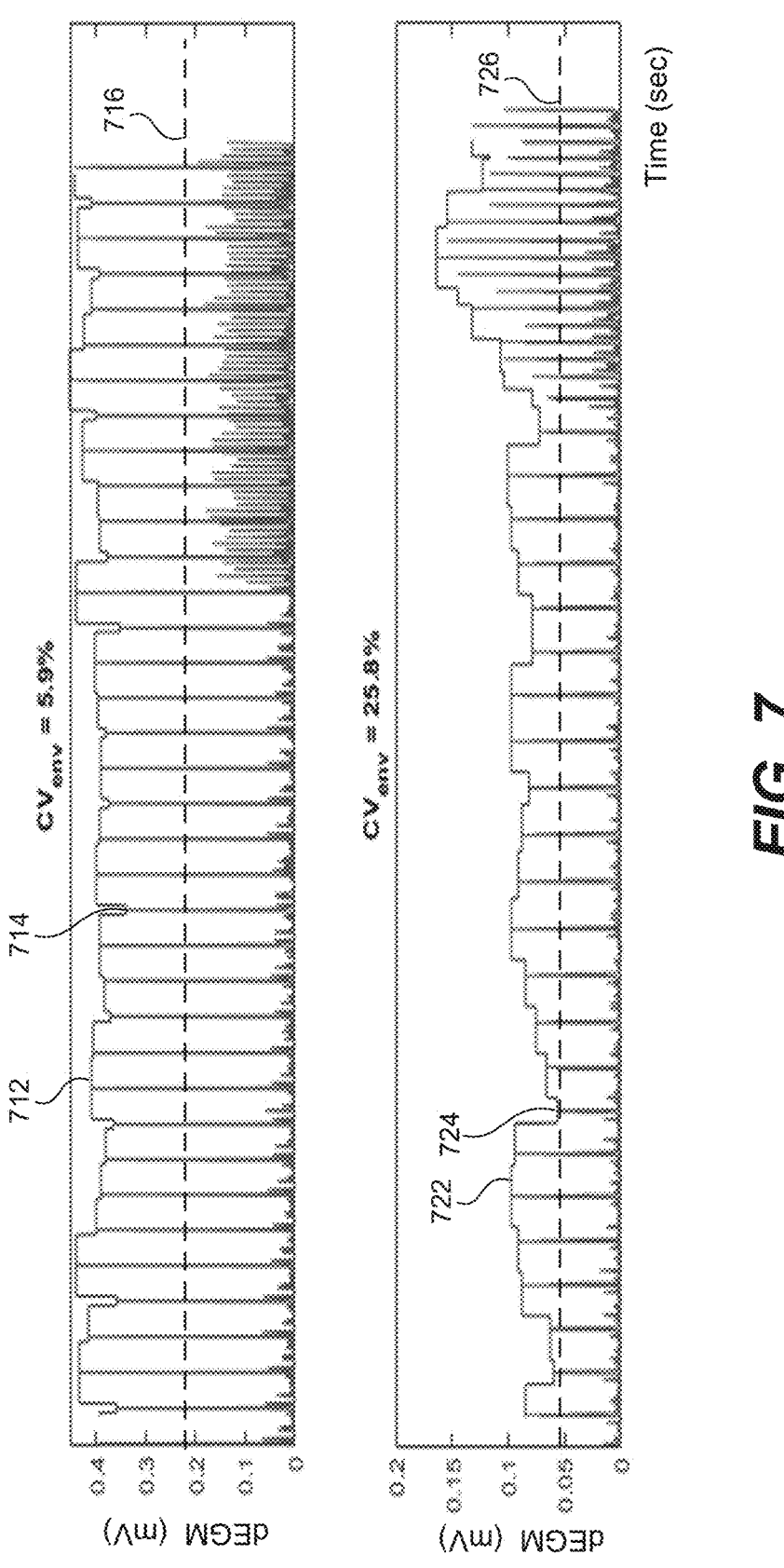
FIG. 7 illustrates example signal envelopes for two different difference signals (e.g., dEGM signals), based upon which a coefficient of variation can be determined and used to specify a signal envelope guided threshold for use in performing R-wave redetections, in accordance with certain embodiments of the present technology.

The flow diagram in FIG. 6 will now be used to explain how the signal envelope guided R-wave detection threshold can be determined at an instance of step 448, which was introduced above in the discussion of FIG. 4B. Referring to FIG. 6, step 602 involves extracting a signal envelope from the difference signal (e.g., the dEGM signal) by identifying a maximum value of the difference signal within a moving window. The length of this moving window can be set to 2, 3, or 4 times the tachycardia cutoff interval, but is not limited thereto, in order to bypass smaller amplitude components, such as noise artifacts and T-wave residuals. Referring briefly to FIG. 7, in the upper panel an example signal envelope from an example difference signal is labeled 712, and in the lower panel an example signal envelope from another example difference signal is labeled 722.

Referring again to FIG. 6, step 604 involves determining a coefficient of variation of the signal envelope. The coefficient of variation is a statistical measure of the dispersion of data points in a data series around the mean, and can be determined by determining the ratio of the standard deviation to the mean. Step 608 involves identifying a minimum value in the signal envelope. Referring briefly again to FIG. 7, the coefficient of variation of the signal envelope 712 in the upper panel is 5.9% and the minimum value in the signal envelope 712 is labeled 714. The coefficient of variation of the signal envelope 722 in the upper panel is 28.8% and the minimum value in the signal envelope 722 is labeled 724. Referring again to FIG. 6, step 608 involves comparing the coefficient of variation of the signal envelope to a corresponding coefficient of variation (COV) threshold. An example COV threshold is 10%, or more generally within the range of 8% to 15%, but is not limited thereto. At step 610 there is a determination of whether the coefficient of variation of the signal envelope is less than the corresponding COV threshold (e.g. 10%). If the answer to the determination at step 610 is Yes, then flow goes to step 612. At step 612, the signal envelope guided R-wave detection threshold is set to the product of a first predetermined value (e.g., 0.65, but not limited thereto) multiplied by the minimum value in the signal envelope, which had been determined at step 606. If the answer to the answer to the determination at step 610 is No (i.e., if the coefficient of variation of the signal envelope is equal to or greater than the corresponding COV threshold), then flow goes to step 614. At step 614, the signal envelope guided R-wave detection threshold is set to the product of a second predetermined value (e.g., 0.85, but not limited thereto) multiplied by the minimum value in the signal envelope, which had been determined at step 606, wherein the second predetermined value is greater than the first predetermined value. Assuming for example that the corresponding COV threshold is 10%, referring again to FIG. 7, in the top panel the coefficient of variation of the signal envelope is 5.9%, which is less than 10%, in which case the signal envelope guided R-wave detection threshold would be set at step 612. By contrast, in the lower panel in FIG. 7 the coefficient of variation of the signal envelope is 25.8%, which is greater than 10%, in which case the signal envelope guided R-wave detection threshold would be set at step 614. While steps 608 and 610 in FIG. 6 are shown as two separate steps, they can be combined into a single step, as would be appreciated by one of skill in the art reviewing the flow diagram.

Referring again to FIG. 7, the dashed line 716 in the top panel illustrates an example of a signal envelope guided R-wave detection threshold set at an instance of step 612. The dashed line 726 in the bottom panel in FIG. 7 illustrates an example of a signal envelope guided R-wave detection threshold set at an instance of step 614. These signal amplitude guided R-wave detection thresholds can be used at instances of step 450 to perform R-wave redetections.

Figure 8:
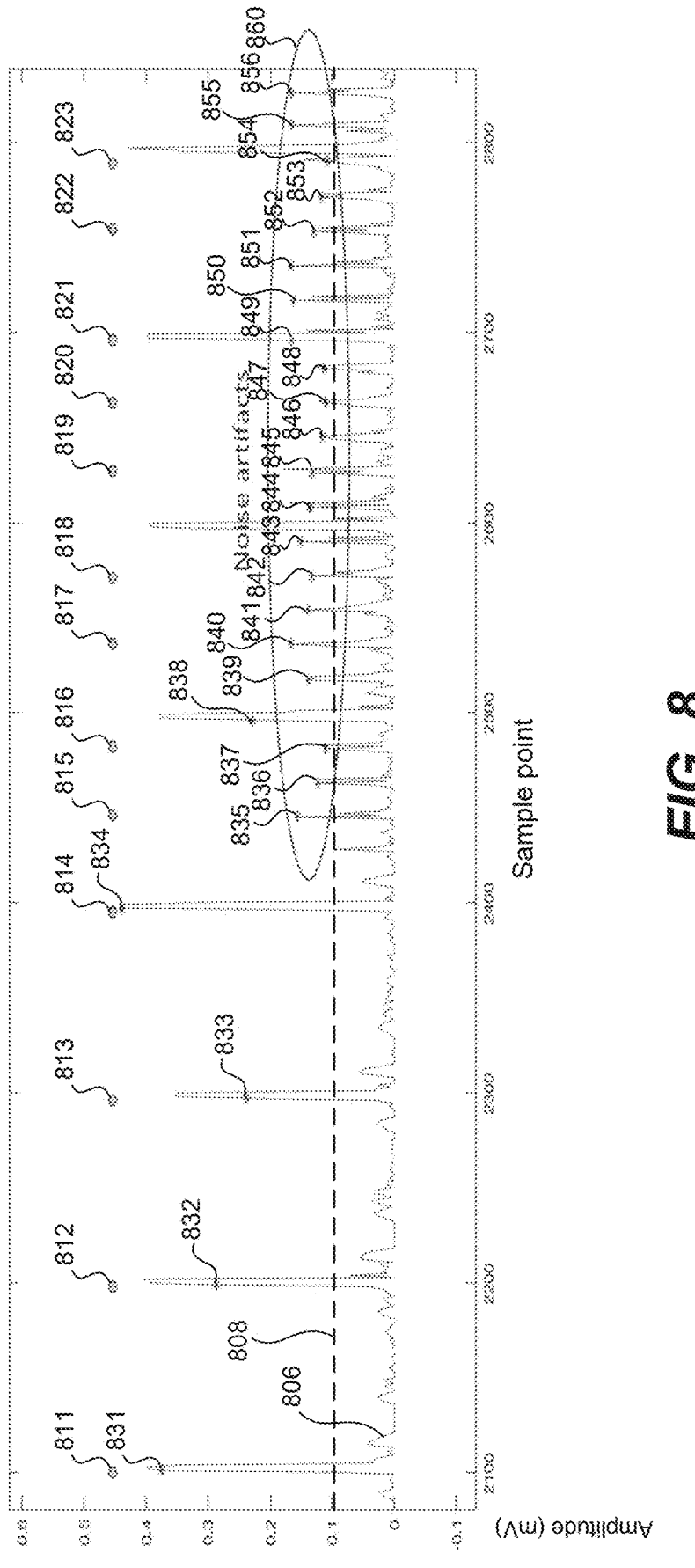
FIG. 8 illustrates how R-wave redetections can be identified at an instance of step 460 in FIG. 4B by comparing an amplitude of a difference signal, or a rectified version thereof, to a minimal sensed R-wave amplitude guided threshold.

FIG. 8 will now be used to show how R-wave redetections can be identified at an instance of step 460 in FIG. 4B by comparing an amplitude of a difference signal (e.g., a dEGM signal) 806, or more specifically a rectified version thereof, to a minimal sensed R-wave amplitude guided threshold 808, wherein the minimal sensed R-wave amplitude guided threshold 808 is determined at an instance of step 459 in FIG. 4B. In FIG. 8, the circles labeled 811 through 823 correspond to R-waves initially detected by comparing a difference signal, i.e., the dEGM signal 806, to an R-wave detection threshold at instances of steps 310 and 312. The stars or asterisks labeled 831 through 856 correspond to redetected R-waves detected by comparing the amplitude of the dEGM signal 806 to the minimal sensed R-wave amplitude guided threshold 808. The redetected R-waves within the oval 860 correspond to noise artifacts, as opposed to true R-waves.

Figure 9:
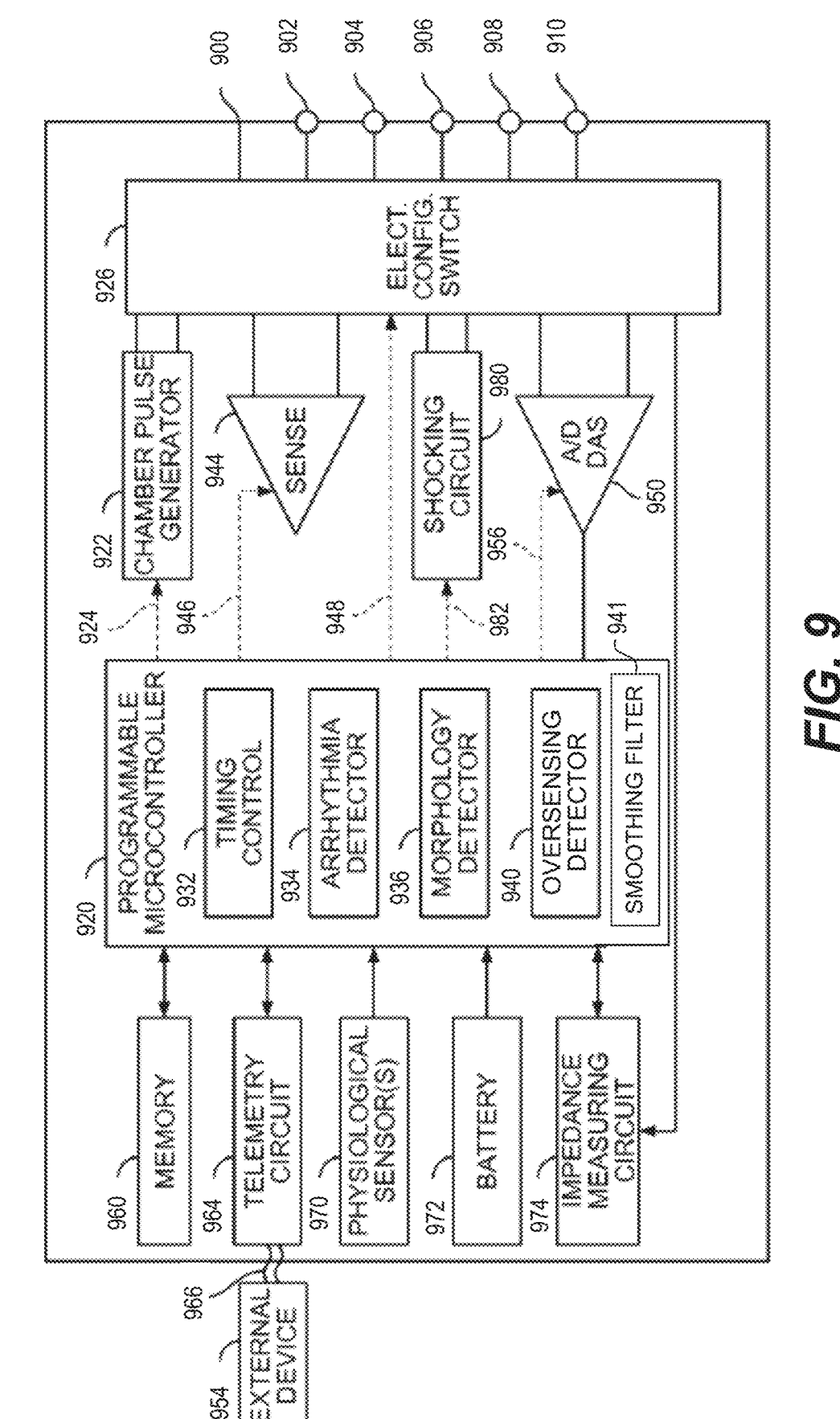
FIG. 9 shows a block diagram of an IMD in accordance with certain embodiments of the present technology.

FIG. 9 shows a block diagram of one embodiment of an IMD that is implanted into a patient in accordance with a certain embodiment of the present technology. The IMD 901 may be implemented as a full-function biventricular pacemaker, equipped with both atrial and ventricular sensing and pacing circuitry for four chamber sensing and stimulation therapy (including both pacing and shock treatment). Optionally, the IMD 901 may provide full-function cardiac resynchronization therapy. Alternatively, the IMD 901 may be implemented with a reduced set of functions and components. For instance, the IMD may be implemented without pacing, e.g., if the IMD is an ICM. The IMD 901 can be coupled to one or more leads for single chamber or multi-chamber pacing and/or sensing. Alternatively, the IMD 901 can be an LCP or ICM that includes electrodes located on or very close to a housing 900 of the IMD 901.

The IMD 901 has a housing 900 to hold the electronic/computing components. The housing 900 (which is often referred to as the "can", "case", "encasing", or "case electrode") may be programmably selected to act as the return electrode for certain stimulus modes. The housing 900 may further include a connector (not shown) with a plurality of terminals 902, 904, 906, 908, and 910. The terminals may be connected to electrodes that are located in various locations on the housing 900 or to electrodes located on leads. The electrodes to which the terminals 902, 904, 906, 908, and 910 are connected can also be referenced, respectively, using reference numbers 902, 904, 906, 908, and 910, and the case electrode can be referenced as case electrode 900. The IMD 901 includes a programmable microcontroller 920 that controls various operations of the IMD 901, including cardiac monitoring and/or stimulation therapy. The microcontroller 920 includes a microprocessor (or equivalent control circuitry), RAM and/or ROM memory, logic and timing circuitry, state machine circuitry, and I/O circuitry.

The IMD 901 further includes a pulse generator 922 that generates stimulation pulses and communication pulses for delivery by two or more electrodes coupled thereto. The pulse generator 922 is controlled by the microcontroller 920 via a control signal 924. The pulse generator 922 may be coupled to the select electrode(s) via an electrode configuration switch 926, which includes multiple switches for connecting the desired electrodes to the appropriate I/O circuits, thereby facilitating electrode programmability. The switch 926 is controlled by a control signal 928 from microcontroller 920.

In the embodiment of FIG. 9, a single pulse generator 922 is illustrated. Optionally, the IMD may include multiple pulse generators, similar to the pulse generator 922, where each pulse generator is coupled to two or more electrodes and controlled by the microcontroller 920 to deliver select stimulus pulse(s) to the corresponding two or more electrodes. Where the IMD does not perform therapy, the pulse gene The microcontroller 920 is illustrated as including timing control circuitry 932 to control the timing of the stimulation pulses (e.g., pacing rate, atrio-ventricular (AV) delay, atrial interconduction (A-A) delay, or ventricular interconduction (V-V) delay, etc.). The timing control circuitry 932 may also be used for the timing of refractory periods, blanking intervals, noise detection windows, evoked response windows, alert intervals, marker channel timing, and so on. The microcontroller 920 also has an arrhythmia detector 934 for detecting arrhythmia conditions and a morphology detector

936. Although not shown, the microcontroller 920 may further include other dedicated circuitry and/or firmware/software components that assist in monitoring various conditions of the patient's heart and managing pacing therapies. The microcontroller 920 is also shown as including an oversensing detector 940, which can be used to perform any of the embodiments of the present technology described above with reference to FIGS. 1A-8. The oversensing detector 940 can more generally be implemented using hardware, software, firmware, and/or combinations thereof. The microcontroller can include a processor. Additionally, the microcontroller 920 is shown as including a smoothing filter 941, which can be a median filter, but is not limited thereto. More generally, a processor of the IMD can digitally implement the smoothing filter 941. It is also possible and within the scope of the embodiments described herein that the smoothing filter 941 be implemented external to the microcontroller 920, e.g., using an application specific integrated circuit (ASIC), a digital signal processor (DSP), or a field programmable gate array (FPGA), or the like. The microcontroller, and/or the processor thereof, can be used to perform the methods of the present technology described herein.

The IMD 901 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 920, or as software/firmware instructions programmed into and executed by the microcontroller 920. Alternatively, the modem may reside separately from the microcontroller as a standalone component.

The IMD 901 includes a sensing circuit 944 selectively coupled to two or more electrodes, that perform sensing operations, through the switch 926 to detect the presence of cardiac activity in the right chambers of the heart. The sensing circuit 944 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 926 determines the sensing polarity of the cardiac signal by selectively closing the appropriate switches. In this way, the clinician may program the sensing polarity independent of the stimulation polarity.

The output of the sensing circuit 944 is connected to the microcontroller 920 which, in turn, triggers or inhibits the pulse generator 922 in response to the presence or absence of cardiac activity. The sensing circuit 944 receives a control signal 946 from the microcontroller 920 for purposes of controlling the gain, threshold, polarization charge removal circuitry (not shown), and the timing of any blocking circuitry (not shown) coupled to the inputs of the sensing circuitry.

In the embodiment of FIG. 9, a single sensing circuit 944 is illustrated. Optionally, the IMD may include multiple sensing circuits, similar to the sensing circuit 944, where each sensing circuit is coupled to two or more electrodes and controlled by the microcontroller 920 to sense electrical activity detected at the corresponding two or more electrodes. The sensing circuit 944 may operate in a unipolar sensing configuration or in a bipolar sensing configuration.

The IMD 901 further includes an analog-to-digital (A/D) data acquisition system (DAS) 950 coupled to two or more electrodes via the switch 926 to sample cardiac signals across any pair of desired electrodes. Data acquisition system 950 is configured to acquire intracardiac electrogram signals, convert the raw analog data into digital data, and store the digital data for later processing and/or telemetric transmission to an external device 954 (e.g., a programmer, local transceiver, or a diagnostic system analyzer). Data acquisition system 950 is controlled by a control signal 956 from the microcontroller 920.

The microcontroller 920 is coupled to a memory 960 by a suitable data/address bus. The programmable operating parameters used by the microcontroller 920 are stored in memory 960 and used to customize the operation of the IMD 901 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 901 may be non-invasively programmed into memory 960 through a telemetry circuit 964 in telemetric communication via a communication link 966 with an external device 954. The telemetry circuit 964 allows intracardiac electrograms and status information relating to the operation of the IMD 901 (as contained in the microcontroller 920 or memory 960) to be sent to the external device 954 through the communication link 966.

The IMD 901 can further include magnet detection circuitry (not shown), coupled to the microcontroller 920, to detect when a magnet is placed over the unit. A magnet may be used by a clinician to perform various test functions of IMD 901 and/or to signal the microcontroller 920 that the external device 954 is in place to receive or transmit data to the microcontroller 920 through the telemetry circuit 964.

The IMD 901 can further include one or more physiological sensors 970. Such sensors are commonly referred to as "rate-responsive" sensors because they are typically used to adjust pacing stimulation rates according to the exercise state of the patient. However, the physiological sensor(s) 970 may further be used to detect changes in cardiac output, changes in the physiological condition of the heart, or diurnal changes in activity (e.g., detecting sleep and wake states). Signals generated by the physiological sensor(s) 970 are passed to the microcontroller 920 for analysis. The microcontroller 920 responds by adjusting the various pacing parameters (such as rate, AV Delay, V-V Delay, etc.) at which the atrial and ventricular pacing pulses are administered. While shown as being included within the IMD 901, one or more physiological sensor(s) 970 may be external to the IMD 901, yet still be implanted within or carried by the patient. Examples of physiologic sensors include sensors that, for example, sense respiration rate, pH of blood, ventricular gradient, activity, position/posture, minute ventilation (MV), and so forth.

A battery 972 provides operating power to all of the components in the IMD 901. The battery 972 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 972 also desirably has a predictable discharge characteristic so that elective replacement time can be detected. As one example, the IMD 901 employs lithium/silver vanadium oxide batteries.

The IMD 901 further includes an impedance measuring circuit 974, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 974 is coupled to the switch 926 so that any desired electrode may be used. In this embodiment the IMD 901 further includes a shocking circuit 980 coupled to the microcontroller 920 by a data/address bus 982.

EXAMPLES

Example 1. An apparatus, comprising: a plurality of electrodes; a sensing circuit coupled to at least two of the electrodes and configured to sense a signal indicative of cardiac electrical activity; a smoothing filter configured to filter the sensed signal indicative of cardiac electrical activity to thereby produce a filtered signal indicative of cardiac electrical activity; difference circuitry configured to produce a difference signal indicative of cardiac electrical activity by determining a difference between the sensed signal indicative of cardiac electrical activity and the filtered signal indicative of cardiac electrical activity; and at least one processor configured to detect a tachycardia based on the difference signal, or configured to determine whether or not to reject a tachycardia detection based on the difference signal.

Example 2. The apparatus of example 1, wherein: the sensed signal indicative of cardiac electrical activity comprises a sensed electrogram (EGM) signal; the filtered signal comprises a filtered EGM (fEGM) signal; the smoothing filter is configured to filter to the sensed EGM signal to produce the filtered EGM (fEGM) signal; the difference circuitry is configured to produce a difference EGM (dEGM) signal indicative of cardiac electrical activity by determining a difference between the sensed EGM signal and the fEGM signal; and the at least one processor is configured to detect a tachycardia based on the dEGM signal, or configured to determine whether or not to reject a tachycardia detection based on the dEGM signal.

Example 3. The apparatus of any one of examples 1 or 2, wherein the smoothing filter comprises a median filter.

Example 4. The apparatus of any one of examples 1 through 3, wherein the at least one processor is configured to: compare an amplitude of the difference signal to an R-wave detection threshold to thereby detect R-waves; determine a heart rate (HR) or R-R intervals based on the detected R-waves; and detect the tachycardia based on the HR or the RR-intervals.

Example 5. The apparatus of any one of examples 1 through 3, wherein the at least one processor is configured to: compare an amplitude of the sensed signal indicative of cardiac electrical activity to an R-wave detection threshold to thereby detecting R-waves; determine a heart rate (HR) or R-R intervals based on the detected R-waves; detect a tachycardia based on the HR or the RR-intervals; and determine whether or not to reject the tachycardia detection based on the difference signal.

Example 6. The apparatus of example 5, wherein the at least one processor is configured to determine whether or not to reject the tachycardia detection based on the difference signal by determining whether the tachycardiac detection was likely due to at least one of T-wave oversensing or noise, and wherein in order to the determine whether the tachycardiac detection was likely due to at least one of T-wave oversensing or noise the at least one processor is configured to: for each detected R-wave of a plurality of R-waves detected by comparing the amplitude of the sensed signal indicative of cardiac electrical activity to the R-wave detection threshold: determine a peak amplitude ratio for the detected R-wave by dividing an absolute value of a peak amplitude of the R-wave within the difference signal by an absolute value of a peak amplitude of the detected R-wave within the sensed signal; compare the peak amplitude ratio to a corresponding peak amplitude ratio (PAR) threshold; and when the peak amplitude ratio is less than the corresponding PAR threshold, analyze windows of the difference signal before and after the detected R-wave to determine whether or not to classify the detected R wave as being falsely detected due to T-wave oversensing; and determine whether or not to reject the tachycardia detection based on an amount of the detected R-waves that were classified as being falsely detected due to T-wave oversensing.

Example 7. The apparatus of example 6, wherein in order to analyze windows of the difference signal before and after a said detected R-wave to determine whether or not to classify the detected R wave as being falsely detected due to T-wave oversensing, the at least one processor is configured to: compare a first window of the difference signal immediately preceding the detected R-wave to a second window of the difference signal immediately following the detected R-wave to determine which one of the first and the second windows has a larger peak amplitude; count a number of reversal points in the one of the first and the second windows of the difference signal that has the larger peak amplitude in the difference signal; compare the number of reversal points to a corresponding number of reversal points (NRP) threshold; and determine whether or not to classify the R-wave as being falsely detected due to T-wave oversensing based on results of the comparing the number of reversal points to the corresponding NRP threshold.

Example 8. The apparatus of example 6 or 7, wherein in order to determine whether or not to reject the tachycardia detection based on an amount of the detected R-waves that were classified as being falsely detected due to T-wave oversensing, the at least one processor is configured to: compare an amount of the detected R-waves, that were initially used to detect the tachycardia and were thereafter classified as being falsely detected due to T-wave oversensing, to a corresponding T-wave oversensing threshold; and reject the tachycardia detection in response to the amount of the R-waves classified as being falsely detected due to T-wave oversensing equaling or exceeding the corresponding T-wave oversensing threshold.

Example 9. The apparatus of any one of examples 6 through 8, wherein the at least one processor is further configured to: mark or classify a tachycardia detection as potentially being a ventricular tachycardia (VT) when at least two consecutive ones of the detected R-waves are classified as being falsely detected due to T-wave oversensing.

Example 10. The apparatus of example 5, wherein in response to none of the R-waves being classified as being falsely detected due to T-wave oversensing, the at least one processor is configured to: determine a signal envelope guided R-wave detection threshold; redetect R-waves in the difference signal by comparing the amplitude of the difference signal to the signal envelope guided R-wave detection threshold; determine a redetected heart rate (HR) or redetected R-R intervals based on the redetected R-waves; and determine whether or not to reject the tachycardia detection based on the redetected HR or the redetected R-R intervals.

Example 11. The apparatus of example 10, wherein in order to determine whether or not to reject the tachycardia detection based on the redetected HR or the redetected R-R intervals, the at least one processor is configured to: compare the redetected HR or an average of the redetect R-R intervals to a corresponding threshold indicative of the redetected HR being too slow to be an actual tachycardia; and selectively reject the tachycardia detection based on results of the comparing the redetected HR or the average of the redetect R-R intervals to the corresponding threshold indicative of the redetected HR being too slow to be a tachycardia.

Example 12. The apparatus of example 10 or 11, wherein in order to determine the signal envelope guided R-wave detection threshold, the at least one processor is configured to: extract a signal envelope from the difference signal by identifying a maximum value of the difference signal within a moving window; determine a coefficient of variation of the signal envelope; identify a minimum value in the signal envelope; compare the coefficient of variation of the signal envelope to a corresponding coefficient of variation (COV) threshold; set the signal envelope guided R-wave detection threshold to a product of a first predetermine value multiplied by the minimum value in the signal envelope, when the coefficient of variation is less than the corresponding COV threshold; and set the signal envelope guided R-wave detection threshold to a product of a second predetermined value multiplied by the minimum value in the signal envelope, when the coefficient of variation is greater than the corresponding COV threshold, wherein the second predetermined value is greater than the first predetermined value.

Example 13. The apparatus of any one of examples 5 through 12, wherein in response to none of the R-waves being classified as being falsely detected due to T-wave oversensing, the at least one processor is configured to: determine a minimal sensed R-wave amplitude guided threshold; redetect R-waves in the difference signal by comparing the amplitude of the difference signal to the minimal sensed R-wave amplitude guided threshold; determine a redetected heart rate (HR) or redetected R-R intervals based on the redetected R-waves; and determine whether or not to reject the tachycardia detection based on the redetected HR or the redetected R-R intervals.

Example 14. The apparatus of example 13, wherein in order to determining whether or not to reject the tachycardia detection based on the redetected HR or the redetected R-R intervals, the at least one processor is configured to: compare the redetected HR or an average of the redetect R-R intervals to a corresponding threshold indicative of the redetected HR being too fast to be an actual tachycardia; and selectively reject the tachycardia detection based on results of the comparing the redetected HR or the average of the redetect R-R intervals to the corresponding threshold indicative of the redetected HR being too fast to be an actual tachycardia.

Example 15. The apparatus of example 14, wherein the at least one processor is configured to: determine the minimal sensed R-wave amplitude guided threshold by identifying a smallest R-wave peak in the difference signal, and setting the minimal sensed R-wave amplitude guided threshold to a value that is less than the smallest R-wave peak in the difference signal; and wherein when redetecting R-waves in the difference signal, by comparing the amplitude of the difference signal to the minimal sensed R-wave amplitude guided threshold, a length of a refractory period that is used for the redetecting is less than a length of a refractory period that is used to initially detect R-waves when comparing the sensed signal indicative of cardiac electrical activity to the R-wave detection threshold.

Example 16. The apparatus of any one of the above examples, further comprising a memory and a telemetry circuit, and wherein the at least one processor is configured to detect a tachycardia based on the difference signal, and in response to the tachycardia being detected, the at least one processor is configured to perform one or more of the following: store or maintain data related to the tachycardia in the memory; cause the telemetry circuit to transmit data related to the tachycardia to another apparatus; or initiate delivery of tachycardia therapy using at least one of the plurality of electrodes.

Example 17. The apparatus of any one of the above examples, further comprising a memory and a telemetry circuit, and wherein the at least one processor is configured to determine whether or not to reject a tachycardia detection based on the difference signal, and in response to the tachycardia detection being rejected, the at least one processor is configured to perform one or more of the following: allow data related to the tachycardia stored in the memory to be overwritten; prevent the telemetry circuit from transmitting data related to the tachycardia to another apparatus; or withhold or terminate tachycardia therapy.

Example 18. A method, comprising: (a) obtaining a sensed signal indicative of cardiac electrical activity; (b) producing a filtered signal indicative of cardiac electrical activity by applying a smoothing filter to the sensed signal indicative of cardiac electrical activity; (c) producing a difference signal indicative of cardiac electrical activity by determining a difference between the sensed signal indicative of cardiac electrical activity and the filtered signal indicative of cardiac electrical activity; and (d) detecting a tachycardia based on the difference signal, or determining whether or not to reject a tachycardia detection based on the difference signal.

Example 19. The method of example 18, wherein: the sensed signal indicative of cardiac electrical activity comprises a sensed electrogram (EGM) signal; step (a) comprising obtaining the sensed EGM signal; step (b) comprises producing a filtered EGM (fEGM) signal by applying a smoothing filter to the sensed EGM signal; step (c) comprises producing a difference EGM (dEGM) signal by determining a difference between the sensed EGM signal and the fEGM signal; and step (d) comprises detecting a tachycardia based on the dEGM signal, or determining whether or not to reject a tachycardia detection based on the dEGM signal.

Example 20. The method of example 18 or 19, wherein the smoothing filter comprises a median filter, and wherein step (b) comprises producing the filtered signal indicative of cardiac electrical activity by applying the median filter to the sensed signal indicative of cardiac electrical activity.

Example 21. The method of any one of examples 18 through 20, wherein step (d) comprising detecting a tachycardia based on the difference signal by: (d.1) comparing an amplitude of the difference signal to an R-wave detection threshold; (d.2) detecting R-waves based on results of the comparing; (d.3) determining a heart rate (HR) or R-R intervals based on the detected R-waves; and (d.4) detecting the tachycardia based on the HR or the RR-intervals.

Example 22. The method of any one of examples 18 through 20, wherein: a tachycardia is detected based on the sensed signal indicative of cardiac electrical activity obtained at step (a) by comparing an amplitude of the sensed signal indicative of cardiac electrical activity to an R-wave detection threshold, detecting R-waves based on results of the comparing, determining a heart rate (HR) or R-R intervals based on the detected R-waves, and detecting the tachycardia based on the HR or the RR-intervals; steps (b), (c) and (d) are performed in response to the tachycardia detection; and step (d) comprises determining whether or not to reject the tachycardia detection based on the difference signal.

Example 23. The method of example 22, wherein the determining whether or not to reject the tachycardia detection based on the difference signal at step (d) includes determining whether the tachycardiac detection was likely due to at least one of T-wave oversensing or noise, and wherein the determining whether the tachycardiac detection was likely due to at least one of T-wave oversensing or noise comprises: (d.1) for each detected R-wave of a plurality of R-waves detected by comparing the amplitude of the sensed signal indicative of cardiac electrical activity to the R-wave detection threshold: determining a peak amplitude ratio for the detected R-wave by dividing an absolute value of a peak amplitude of the R-wave within the difference signal by an absolute value of a peak amplitude of the detected R-wave within the sensed signal; comparing the peak amplitude ratio to a corresponding peak amplitude ratio (PAR) threshold; and when the peak amplitude ratio is less than the corresponding PAR threshold, analyzing windows of the difference signal before and after the detected R-wave to determine whether or not to classify the detected R wave as being falsely detected due to T-wave oversensing; and (d.2) determining whether or not to reject the tachycardia detection based on an amount of the detected R-waves that were classified as being falsely detected due to T-wave oversensing.

Example 24. The method of example 23, wherein step (d.1) further comprises for a said detected R-wave, in response to the peak amplitude ratio for the detected R-wave being less than the corresponding PAR threshold: comparing a first window of the difference signal immediately preceding the detected R-wave to a second window of the difference signal immediately following the detected R-wave to determine which one of the first and the second windows has a larger peak amplitude; counting a number of reversal points in the one of the first and the second windows of the difference signal that has the larger peak amplitude in the difference signal; comparing the number of reversal points to a corresponding number of reversal points (NRP) threshold; and determining whether or not to classify the R-wave as being falsely detected due to T-wave oversensing based on results of the comparing the number of reversal points to the corresponding NRP threshold.

Example 25. The method of example 23 or 24, wherein step (d.2) comprises: comparing an amount of the detected R-waves, that were initially used to detect the tachycardia and were thereafter classified as being falsely detected due to T-wave oversensing, to a corresponding T-wave oversensing threshold; and rejecting the tachycardia detection in response to the amount of the R-waves classified as being falsely detected due to T-wave oversensing equaling or exceeding the corresponding T-wave oversensing threshold.

Example 26. The method of any one of examples 23 through 25, further comprising: (d.3) marking or classifying a tachycardia detection as potentially being a ventricular tachycardia (VT) when at least two consecutive ones of the detected R-waves are classified as being falsely detected due to T-wave oversensing.

Example 27. The method of example 22, wherein in response to none of the R-waves being classified as being falsely detected due to T-wave oversensing, the method further comprises: determining a signal envelope guided R-wave detection threshold; redetecting R-waves in the difference signal by comparing the amplitude of the difference signal to the signal envelope guided R-wave detection threshold; determining a redetected heart rate (HR) or redetected R-R intervals based on the redetected R-waves; and determining whether or not to reject the tachycardia detection based on the redetected HR or the redetected R-R intervals.

Example 28. The method of example 27, wherein the determining whether or not to reject the tachycardia detection based on the redetected HR or the redetected R-R intervals comprises: comparing the redetected HR or an average of the redetect R-R intervals to a corresponding threshold indicative of the redetected HR being too slow to be an actual tachycardia; and selectively rejecting the tachycardia detection based on results of the comparing the redetected HR or the average of the redetect R-R intervals to the corresponding threshold indicative of the redetected HR being too slow to be a tachycardia.

Example 29. The method of example 27 or 28, wherein the determining the signal envelope guided R-wave detection threshold comprises: extracting a signal envelope from the difference signal by identifying a maximum value of the difference signal within a moving window; determining a coefficient of variation of the signal envelope; identifying a minimum value in the signal envelope; comparing the coefficient of variation of the signal envelope to a corresponding coefficient of variation (COV) threshold; setting the signal envelope guided R-wave detection threshold to a product of a first predetermine value multiplied by the minimum value in the signal envelope, when the coefficient of variation is less than the corresponding COV threshold; and setting the signal envelope guided R-wave detection threshold to a product of a second predetermined value multiplied by the minimum value in the signal envelope, when the coefficient of variation is greater than the corresponding COV threshold, wherein the second predetermined value is greater than the first predetermined value.

Example 30. The method of any one of examples 22 through 29, wherein in response to none of the R-waves being classified as being falsely detected due to T-wave oversensing, the method further comprises: determining a minimal sensed R-wave amplitude guided threshold; redetecting R-waves in the difference signal by comparing an amplitude of the difference signal to the minimal sensed R-wave amplitude guided threshold; determining a redetected heart rate (HR) or redetected R-R intervals based on the redetected R-waves; and determining whether or not to reject the tachycardia detection based on the redetected HR or the redetected R-R intervals.

Example 31. The method of example 30, wherein the determining whether or not to reject the tachycardia detection based on the redetected HR or the redetected R-R intervals comprises: comparing the redetected HR or an average of the redetect R-R intervals to a corresponding threshold indicative of the redetected HR being too fast to be an actual tachycardia; and selectively rejecting the tachycardia detection based on results of the comparing the redetected HR or the average of the redetect R-R intervals to the corresponding threshold indicative of the redetected HR being too fast to be an actual tachycardia.

Example 32. The method of example 31, wherein: the determining the minimal sensed R-wave amplitude guided threshold comprises identifying a smallest R-wave peak in the difference signal, and setting the minimal sensed R-wave amplitude guided threshold to a value that is less than the smallest R-wave peak in the difference signal; and when redetecting R-waves in the difference signal, by comparing an amplitude of the difference signal to the minimal sensed R-wave amplitude guided threshold, a length of a refractory period that is used for the redetecting is less than a length of a refractory period that is used to initially detect R-waves at step (a) when comparing the amplitude of the sensed signal indicative of cardiac electrical activity to the R-wave detection threshold.

Example 33. The method of any one of the above examples, wherein step (d) comprises detecting a tachycardia based on the difference signal, and further comprising performing one or more of the following in response to the tachycardia being detected: storing or maintaining data related to the tachycardia in memory; causing transmitting of data related to the tachycardia to another apparatus; or initiating delivery of tachycardia therapy.

Example 34. The method of any one of the above examples, wherein step (d) comprises determining whether or not to reject a tachycardia detection based on the difference signal, and further comprising performing one or more of the following in response to the tachycardia detection being rejected: allowing data related to the tachycardia stored in memory to be overwritten; preventing transmitting of data related to the tachycardia to another apparatus; or withholding or terminating tachycardia therapy.

The embodiments of the present technology described above were primarily described as being used with an implantable medical device or system that monitors for tachycardias. Such embodiments of the present technology can alternatively be used with a non-implantable device or system (aka an external device or system) that includes at least two electrodes in contact with a person's skin and is used to monitor HR and/or for one or more types of arrhythmic episodes based on sensed intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuitry coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for a tachycardia and/or other types of arrythmia(s) and determine when there is a false positive detection. Additionally, or alternatively, such a user wearable device (or more generally an external device or system) can monitor a person's HR and determine when measures of HR are likely inaccurate due to T-wave oversensing and/or noise. A user wearable device can both obtain a signal indicative of electrical activity of a patient's heart and monitor a person's HR and/or for arrythmia(s) based on intervals obtained from the obtained signal. Alternatively, a user wearable device can be communicatively coupled to another external device, such as a smartphone or tablet computer, and the other external device can obtain the signal from the user wearable device and monitor a person's HR and/or for tachycardias and other types of arrythmia(s) based on intervals. The user wearable device or other external device or system can determine when there may be a false positive and/or when a measured HR may be inaccurate due to oversensing. Other implementations of such an external device or system are also possible and within the scope of the embodiments described herein. It is noted that the term apparatus, as used herein, is intended to cover an IMD, or a non-implanted device such as an external programmer or a user wearable device, as well as a distributed apparatus, e.g., a system.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

What is claimed is:

1. An apparatus, comprising:
   a plurality of electrodes;
   a sensing circuit coupled to at least two of the electrodes and configured to sense a signal indicative of cardiac electrical activity;
   at least one processor configured to detect R-waves based on the sensed signal indicative of cardiac electrical activity and detect a tachycardia based on the R-waves;
   a smoothing filter configured to filter the sensed signal indicative of cardiac electrical activity to thereby produce a filtered signal indicative of cardiac electrical activity; and
   difference circuitry configured to produce a difference signal indicative of cardiac electrical activity by determining a difference between the sensed signal indicative of cardiac electrical activity that has not been filtered by the smoothing filter and the filtered signal indicative of cardiac electrical activity that has been filtered by the smoothing filter; and
   the at least one processor also configured to redetect R-waves based on the difference signal in response to the tachycardia detection, and determine based on the redetected R-waves whether or not to reject the tachycardia detection.

2. The apparatus of claim 1, wherein:
   the sensed signal indicative of cardiac electrical activity comprises a sensed electrogram (EGM) signal;
   the filtered signal comprises a filtered EGM (fEGM) signal;
   the smoothing filter is configured to filter to the sensed EGM signal to produce the filtered EGM (fEGM) signal;
   the difference circuitry is configured to produce a difference EGM (dEGM) signal indicative of cardiac electrical activity by determining a difference between the sensed EGM signal and the fEGM signal; and
   the at least one processor is configured to redetect R-waves based on the dEGM signal in response to the tachycardia detection, and determine whether or not to reject the tachycardia detection based on the redetected R-waves.

3. The apparatus of claim 1, wherein the smoothing filter comprises a median filter.

4. The apparatus of claim 1, wherein the at least one processor is configured to:

compare an amplitude of the difference signal to an R-wave detection threshold to thereby redetect R-waves;

determine a heart rate (HR) or R-R intervals based on the redetected R-waves; and determine whether or not to reject the tachycardia detection based on the HR or the R-R intervals determined based on the redetected R-waves.

5. The apparatus of claim 1, wherein the at least one processor is configured to:

compare an amplitude of the sensed signal indicative of cardiac electrical activity to an R-wave detection threshold to thereby detect R-waves;

determine a heart rate (HR) or R-R intervals based on the detected R-waves;

detect the tachycardia based on the HR or the R-R intervals; and produce the redetect the R-waves in response to the tachycardia detection.

6. The apparatus of claim 5, wherein the at least one processor is configured to determine whether or not to reject the tachycardia detection by determining whether the tachycardia detection was likely due to at least one of T-wave oversensing or noise, and wherein in order to the determine whether the tachycardia detection was likely due to at least one of T-wave oversensing or noise the at least one processor is configured to:

for each detected R-wave of a plurality of R-waves detected by comparing the amplitude of the sensed signal indicative of cardiac electrical activity to the R-wave detection threshold:

determine a peak amplitude ratio for the detected R-wave by dividing an absolute value of a peak amplitude of the redetected R-wave within the difference signal by an absolute value of a peak amplitude of the detected R-wave within the sensed signal;

compare the peak amplitude ratio to a corresponding peak amplitude ratio (PAR) threshold; and when the peak amplitude ratio is less than the corresponding PAR threshold, analyze windows of the difference signal before and after the detected R-wave to determine whether or not to classify the detected R-wave as being falsely detected due to T-wave oversensing; and determine whether or not to reject the tachycardia detection based on an amount of the detected R-waves that were classified as being falsely detected due to T-wave oversensing.

7. The apparatus of claim 6, wherein in order to analyze windows of the difference signal before and after a said detected R-wave to determine whether or not to classify the detected R-wave as being falsely detected due to T-wave oversensing, the at least one processor is configured to:

compare a first window of the difference signal immediately preceding the detected R-wave to a second window of the difference signal immediately following the detected R-wave to determine which one of the first and the second windows has a larger peak amplitude;

count a number of reversal points in the one of the first and the second windows of the difference signal that has the larger peak amplitude in the difference signal;

compare the number of reversal points to a corresponding number of reversal points (NRP) threshold; and determine whether or not to classify the R-wave as being falsely detected due to T-wave oversensing based on results of the comparing the number of reversal points to the corresponding NRP threshold.

8. The apparatus of claim 6, wherein in order to determine whether or not to reject the tachycardia detection based on an amount of the detected R-waves that were classified as being falsely detected due to T-wave oversensing, the at least one processor is configured to:

compare an amount of the detected R-waves, that were initially used to detect the tachycardia and were thereafter classified as being falsely detected due to T-wave oversensing, to a corresponding T-wave oversensing threshold; and reject the tachycardia detection in response to the amount of the R-waves classified as being falsely detected due to T-wave oversensing equaling or exceeding the corresponding T-wave oversensing threshold.

9. The apparatus of claim 6, wherein the at least one processor is further configured to:

mark or classify a tachycardia detection as potentially being a ventricular tachycardia (VT) when at least two consecutive ones of the detected R-waves are classified as being falsely detected due to T-wave oversensing.

10. The apparatus of claim 5, wherein in response to none of the R-waves being classified as being falsely detected due to T-wave oversensing, the at least one processor is configured to:

determine a signal envelope guided R-wave detection threshold;

redetect R-waves in the difference signal by comparing the amplitude of the difference signal to the signal envelope guided R-wave detection threshold;

determine a redetected heart rate (HR) or redetected R-R intervals based on the redetected R-waves; and determine whether or not to reject the tachycardia detection based on the redetected HR or the redetected R-R intervals.

11. The apparatus of claim 10, wherein in order to determine whether or not to reject the tachycardia detection based on the redetected HR or the redetected R-R intervals, the at least one processor is configured to:

compare the redetected HR or an average of the redetect R-R intervals to a corresponding threshold indicative of the redetected HR being too slow to be an actual tachycardia; and selectively reject the tachycardia detection based on results of the comparing the redetected HR or the average of the redetect R-R intervals to the corresponding threshold indicative of the redetected HR being too slow to be a tachycardia.

12. The apparatus of claim 10, wherein in order to determine the signal envelope guided R-wave detection threshold, the at least one processor is configured to:

extract a signal envelope from the difference signal by identifying a maximum value of the difference signal within a moving window;

determine a coefficient of variation of the signal envelope;

identify a minimum value in the signal envelope;

compare the coefficient of variation of the signal envelope to a corresponding coefficient of variation (COV) threshold;

set the signal envelope guided R-wave detection threshold to a product of a first predetermined value multiplied by the minimum value in the signal envelope, when the coefficient of variation is less than the corresponding COV threshold; and set the signal envelope guided R-wave detection threshold to a product of a second predetermined value multiplied by the minimum value in the signal envelope, when the coefficient of variation is greater than the corresponding COV threshold, wherein the second predetermined value is greater than the first predetermined value.

13. The apparatus of claim 5, wherein in response to none of the R-waves being classified as being falsely detected due to T-wave oversensing, the at least one processor is configured to:

determine a minimal sensed R-wave amplitude guided threshold;

redetect R-waves in the difference signal by comparing the amplitude of the difference signal to the minimal sensed R-wave amplitude guided threshold;

determine a redetected heart rate (HR) or redetected R-R intervals based on the redetected R-waves; and determine whether or not to reject the tachycardia detection based on the redetected HR or the redetected R-R intervals.

14. The apparatus of claim 13, wherein in order to determine whether or not to reject the tachycardia detection based on the redetected HR or the redetected R-R intervals, the at least one processor is configured to:

compare the redetected HR or an average of the redetect R-R intervals to a corresponding threshold indicative of the redetected HR being too fast to be an actual tachycardia; and selectively reject the tachycardia detection based on results of the comparing the redetected HR or the average of the redetect R-R intervals to the corresponding threshold indicative of the redetected HR being too fast to be an actual tachycardia.

15. The apparatus of claim 14, wherein the at least one processor is configured to:

determine the minimal sensed R-wave amplitude guided threshold by identifying a smallest R-wave peak in the difference signal, and setting the minimal sensed R-wave amplitude guided threshold to a value that is less than the smallest R-wave peak in the difference signal; and wherein when redetecting R-waves in the difference signal, by comparing the amplitude of the difference signal to the minimal sensed R-wave amplitude guided threshold, a length of a refractory period that is used for the redetecting is less than a length of a refractory period that is used to initially detect R-waves when comparing the sensed signal indicative of cardiac electrical activity to the R-wave detection threshold.

16. The apparatus of claim 1, further comprising a memory and a telemetry circuit, and wherein the at least one processor is configured to detect a tachycardia based on the difference signal, and in response to the tachycardia being detected, the at least one processor is configured to perform one or more of the following:

store or maintain data related to the tachycardia in the memory;

cause the telemetry circuit to transmit data related to the tachycardia to another apparatus; or initiate delivery of tachycardia therapy using at least one of the plurality of electrodes.

17. The apparatus of claim 1, further comprising a memory and a telemetry circuit, and wherein the at least one processor is configured to determine whether or not to reject a tachycardia detection based on the difference signal, and in response to the tachycardia detection being rejected, the at least one processor is configured to perform one or more of the following:

allow data related to the tachycardia stored in the memory to be overwritten;

prevent the telemetry circuit from transmitting data related to the tachycardia to another apparatus; or withhold or terminate tachycardia therapy.

18. A method, comprising:

(a) obtaining a sensed signal indicative of cardiac electrical activity;

(b) detecting R-waves based on the sensed signal indicative of cardiac electrical activity;

(c) detecting a tachycardia based on the R-waves;

(d) producing a filtered signal indicative of cardiac electrical activity by applying a smoothing filter to the sensed signal indicative of cardiac electrical activity;

(e) producing a difference signal indicative of cardiac electrical activity by determining a difference between the sensed signal indicative of cardiac electrical activity that has not been filtered by the smoothing filter and the filtered signal indicative of cardiac electrical activity that has been filtered by the smoothing filter;

(f) in response to the tachycardia being detected, redetecting R-waves based on the difference signal; and (g) determining whether or not to reject the tachycardia detection based on the redetected R-waves.

19. The method of claim 18, wherein:

the sensed signal indicative of cardiac electrical activity comprises a sensed electrogram (EGM) signal;

step (a) comprises obtaining the sensed EGM signal;

step (d) comprises producing a filtered EGM (fEGM) signal by applying the smoothing filter to the sensed EGM signal;

step (e) comprises producing a difference EGM (dEGM) signal by determining a difference between the sensed EGM signal and the fEGM signal; and step (f) comprises redetecting the R-waves based on the dEGM signal.

20. The method of claim 18, wherein the smoothing filter comprises a median filter, and wherein step (d) comprises producing the filtered signal indicative of cardiac electrical activity by applying the median filter to the sensed signal indicative of cardiac electrical activity.

21. The method of claim 18, wherein step (d) comprises:

comparing an amplitude of the sensed signal indicative of cardiac electrical activity to an R-wave detection threshold to thereby detect R-waves;

determining a heart rate (HR) or R-R intervals based on the detected R-waves;

detecting the tachycardia based on the HR or the R-R intervals; and producing the redetect the R-waves in response to the tachycardia detection.

22. The method of claim 21, wherein the determining whether or not to reject the tachycardia detection comprises determining whether the tachycardia detection was likely due to at least one of T-wave oversensing or noise, and wherein in order to the determine whether the tachycardia detection was likely due to at least one of T-wave oversensing or noise the method comprises:

for each detected R-wave of a plurality of R-waves detected by comparing the amplitude of the sensed signal indicative of cardiac electrical activity to the R-wave detection threshold:

determining a peak amplitude ratio for the detected R-wave by dividing an absolute value of a peak amplitude of the R-wave within the difference signal by an absolute value of a peak amplitude of the detected R-wave within the sensed signal;

comparing the peak amplitude ratio to a corresponding peak amplitude ratio (PAR) threshold; and when the peak amplitude ratio is less than the corresponding PAR threshold, analyzing windows of the difference signal before and after the detected R-wave to determine whether or not to classify the detected R-wave as being falsely detected due to T-wave oversensing; and determining whether or not to reject the tachycardia detection based on an amount of the detected R-waves that were classified as being falsely detected due to T-wave oversensing.

23. The method of claim 21, wherein in response to none of the R-waves being classified as being falsely detected due to T-wave oversensing, the method comprises:

determining a signal envelope guided R-wave detection threshold;

redetecting R-waves in the difference signal by comparing the amplitude of the difference signal to the signal envelope guided R-wave detection threshold;

determining a redetected heart rate (HR) or redetected R-R intervals based on the redetected R-waves; and determining whether or not to reject the tachycardia detection based on the redetected HR or the redetected R-R intervals.

\* \* \* \* \*